(12) United States Patent
Xu et al.

(10) Patent No.: US 11,982,662 B2
(45) Date of Patent: May 14, 2024

(54) MARKER FOR SCREENING AND IDENTIFYING NOT-FROM-CONCENTRATE APPLE JUICE BASED ON NON-TARGETED METABOLOMICS AND USE THEREOF

(71) Applicants: INSTITUTE OF QUALITY STANDARD AND TESTING TECHNOLOGY FOR AGRO PRODUCTS OF CAAS, Beijing (CN); SDIC ZHONGLU FRUIT JUICE CO., LTD., Beijing (CN)

(72) Inventors: Zhenzhen Xu, Beijing (CN); Lei Xu, Beijing (CN); Jiming Zhang, Beijing (CN); Chuanzhu Leng, Beijing (CN); Xue Wang, Beijing (CN); Kewen Wang, Beijing (CN); Gang Xin, Beijing (CN); Xinfei Song, Beijing (CN)

( * ) Notice: Subject to any disclaimer, the term of this patent is extended or adjusted under 35 U.S.C. 154(b) by 567 days.

(21) Appl. No.: 17/212,204

(22) Filed: Mar. 25, 2021

(65) Prior Publication Data
US 2022/0187267 A1    Jun. 16, 2022

(30) Foreign Application Priority Data
Dec. 16, 2020    (CN) .................. 202011490243.X

(51) Int. Cl.
  *G01N 33/02*    (2006.01)
(52) U.S. Cl.
  CPC .............................. *G01N 33/025* (2013.01)

(58) Field of Classification Search
  CPC ........ G01N 30/34; G01N 30/72; G01N 30/86; G01N 30/88; G01N 33/025; H01J 49/26
  See application file for complete search history.

(56) References Cited

FOREIGN PATENT DOCUMENTS

| CN | 104730174 A | 6/2015 |
| CN | 111413445 A | 7/2020 |
| CN | 111537644 A | 8/2020 |

OTHER PUBLICATIONS

Diaz-Garcia et al., "Quantification by UHPLC of total individual polyphenols in fruit juices", Food Chemistry 138 (2013) 938-949 (Year: 2013).*

Xu et al, "Integrating untargeted metabolomics and targeted analysis for not from concentrate and from concentrate orange juices discrimination and authentication", Food Chemistry 329 (2020) 127130. (Year: 2020).*

(Continued)

*Primary Examiner* — Jennifer Wecker

(57) ABSTRACT

The present disclosure discloses a marker for screening and distinguishing NFC apple juice based on non-targeted metabolomics and use thereof, relating to the technical field of distinguishing of juice. The marker for distinguishing NFC apple juice disclosed in the present disclosure is selected from the following molecules: gallocatechin, catechin, taxifolin, p-hydroxybenzaldehyde, 5-methoxysalicylic acid, azelaic acid, caffeic acid, chlorogenic acid, epicatechin, eriodictyol, ferulic acid, isoquercitrin, naringenin, n-fructosyl isoleucine, p-coumaraldehyde, p-coumaric acid, phloretin, phlorizin, procyanidin B1, quercetin-3-O-galactoside and rutin. The above markers may be used for distinguishing the NFC apple juice and the FC apple juice, and have relatively high accuracy.

6 Claims, 30 Drawing Sheets

(56) References Cited

OTHER PUBLICATIONS

Liu et al, "Cultivar classification of cloudy apple juices from substandard fruits in China based on aroma profile analyzed by HS-SPME/GC-MS", LWT—Food Science and Technology 102 (2019) 304-309. (Year: 2019).*

Tian et al., "Multivariate Data Analysis of the Physicochemical and Phenolic Properties of Not from Concentrate Apple Juices to Explore the Alternative Cultivars in Juice Production", Food Analytical Methods (2018) 11:1735-1747 (Year: 2018).*

Włodarska et al, "Authentication of apple juice categories based on multivariate analysis of the synchronous fluorescence spectra", Food Control 86 (2018) 42-49. (Year: 2018).*

Bizjak Bat et al, "Primary and secondary metabolites as a tool for differentiation of apple juice according to cultivar and geographical origin", LWT—Food Science and Technology 90 (2018) 238-245. (Year: 2018).*

Willems et al, "Analysis of a series of chlorogenic acid isomers using differential ion mobility and tandem mass spectrometry", Analytica Chimica Acta 933 (2016) 164-174. (Year: 2016).*

Gou et al., Analyses of Physicochemical Properties of NFC Apple Juices from Sixteen Cultivars, College of Food Engineering and Nutritional Science, China Academic Journal Electronic Publishing House, 2018, pp. 800-810.

Guangming, et al., Determination of Phloridzin Content in Apple and Study on the Application of Phloridzin in Apple Juice Quality Control, China Academic Journal Electronic Publishing House, 2010, vol. 10, No. 2.

Tian et al., Changes in teh Physicochemical Properties Aromas and Polyphenols of not from Concentrate (NFC) Apple Juice During Production, CyTA—Journal of Food, 16:1, 755-764, 2018.

Tian et al., Multivariate Data Analysis of the Physicochemical and Phenolic Properties of Not for Concentrate Apple Juices to Explore the Alternative Cultivars in Juice Production, Food Analytical Methods, pp. 1735-1747, 2018.

Chinese Office Action issued in corresponding application No. CN202011490243.X, dated Apr. 6, 2022.

Chinese Notice of Grant issued in corresponding application No. CN202011490243.X, dated May 25, 2022.

* cited by examiner

MARKER FOR SCREENING AND IDENTIFYING NOT-FROM-CONCENTRATE APPLE JUICE BASED ON NON-TARGETED METABOLOMICS AND USE THEREOF

CROSS-REFERENCE TO RELATED APPLICATIONS

The present disclosure claims priority to Chinese Patent Application No. 202011490243.X, filed with the Chinese Patent Office on Dec. 16, 2020, entitled "Marker for Screening and Identifying Not-From-Concentrate Apple Juice Based on Non-targeted Metabolomics and Use thereof", which is incorporated herein by reference in its entirety.

TECHNICAL FIELD

The present disclosure relates to the technical field of distinguishing of concealed adulteration of fruit juice, in particular, to a marker for screening and identifying not-from-concentrate (NFC) apple juice based on non-targeted metabolomics and use thereof.

BACKGROUND ART

With the enhancement of people's consumption consciousness and the improvement on living level, people's pursuit for diet has changed into more attention to the taste, nutrition and convenience of food. Therefore, it is an important subject in the field of food processing to improve the quality of the food product, effectively prevent the quality safety change during the food product processing, and satisfy the consumers' growing consumption demand for high quality food products.

The fruit juice has a wide market due to its good mouthfeel, rich content of vitamins and the like, and convenience for drinking. The consumers are very concerned about the existence of natural ingredients, the existence of effective nutrients, and the green/organic certification in fruit and vegetable juice. With the upgrading of consumption at home and abroad, the types of juice are becoming more and more abundant. Meanwhile, conventional fruit juice from concentrated (FC fruit juice) cannot sufficiently satisfy people's requirements for high quality fruit juice. Therefore, in contrast to the FC fruit juice, the NFC fruit juice becomes the mainstream direction of the current market development. However, on the other hand, as the raw material production and supply and sale of the fruit juice products is increasingly complicated, adulteration and food fraud driven by economic interests are intensified. There are mainly two categories for the form of adulteration of NFC apple juice products, wherein the first one is to blend low-cost juice into high value-added juice; and the second one is to use FC apple juice to pretend to be NFC apple juice.

However, there are currently no markers or relevant technical means for effectively distinguishing the NFC apple juice and the FC apple juice.

In view of this, the present disclosure is specifically proposed.

SUMMARY

The present disclosure is realized as follows:

In one aspect, the present disclosure provides a marker for distinguishing NFC apple juice and FC apple juice, which is at least one selected from the following molecules: gallocatechin, catechin, taxifolin, p-hydroxybenzaldehyde, 5-methoxysalicylic acid, azelaic acid, caffeic acid, chlorogenic acid, epicatechin, eriodictyol, ferulic acid, isoquercitrin, naringenin, n-fructosyl isoleucine, p-coumaraldehyde, p-coumaric acid, phloretin, phlorizin, procyanidin B1, quercetin-3-O-galactoside and rutin.

In another aspect, the present disclosure provides a method for distinguishing NFC apple juice and FC apple juice, wherein the method comprises:
detecting a content of the marker according to claim 1 in an apple juice sample to be distinguished; and judging whether the apple juice sample to be distinguished is NFC apple juice or FC apple juice according to the content of the marker.

BRIEF DESCRIPTION OF DRAWINGS

In order to more clearly illustrate technical solutions of examples of the present disclosure, accompanying drawings which need to be used in the examples will be introduced briefly below. It should be understood that the accompanying drawings below merely show some examples of the present disclosure, therefore, they should not be considered as limitation to the scope, and a person ordinarily skilled in the art still could obtain other relevant figures according to these accompanying drawings, without using any inventive efforts.

FIG. 7-1 is a mirror image of gallocatechin in the negative ion mode.

FIG. 7-2 is a mirror image of catechin in the negative ion mode.

FIG. 7-3 is a mirror image of 5-methoxysalicylic acid in the negative ion mode.

FIG. 7-4 is a mirror image of azelaic acid in the negative ion mode.

FIG. 7-5 is a mirror image of caffeic acid in the positive ion mode.

FIG. 7-6 is a mirror image of chlorogenic acid in the positive ion mode.

FIG. 7-7 is a mirror image of epicatechin in the negative ion mode.

FIG. 7-8 is a mirror image of eriodictyol in the negative ion mode.

FIG. 7-9 is a mirror image of ferulic acid in the negative ion mode.

FIG. 7-10 is a mirror image of isoquercitrin in the negative ion mode.

FIG. 7-11 is a mirror image of naringenin in the negative ion mode.

FIG. 7-12 is a mirror image of n-fructosyl isoleucine in the positive ion mode.

FIG. 7-13 is a mirror image of p-coumaraldehyde in the negative ion mode.

FIG. 7-14 is a mirror image of p-coumaric acid in the positive ion mode.

FIG. 7-15 is a mirror image of phloretin in the negative ion mode.

FIG. 7-16 is a mirror image of phlorizin in the negative ion mode.

FIG. 7-17 is a mirror image of p-hydroxybenzaldehyde in the negative ion mode.

FIG. 7-18 is a mirror image of procyanidin B1 in the negative ion mode.

FIG. 7-19 is a mirror image of quercetin-3-O-galactoside the negative ion mode.

FIG. 7-20 is a mirror image of rutin in the negative ion mode.

FIG. 7-21 is a mirror image of taxifolin in the negative ion mode.

FIG. 8 shows discrimination results of a distinguishing model constructed by accumulating marker data in the positive ion mode in Examples 2 and 3, wherein the accuracy of a correction set and a prediction set reaches 95% and 94%, respectively.

FIG. 9 shows discrimination results of the distinguishing model constructed by accumulating the marker data in the negative ion mode in Examples 2 and 3, wherein the accuracy of a correction set and a prediction set reaches 88% and 88%, respectively; and FIG. 10 is a total ion current distribution diagram of SWATH window in the positive and negative ion modes, A: negative ion mode, and B: positive ion mode.

DETAILED DESCRIPTION OF EMBODIMENTS

Figure 1:
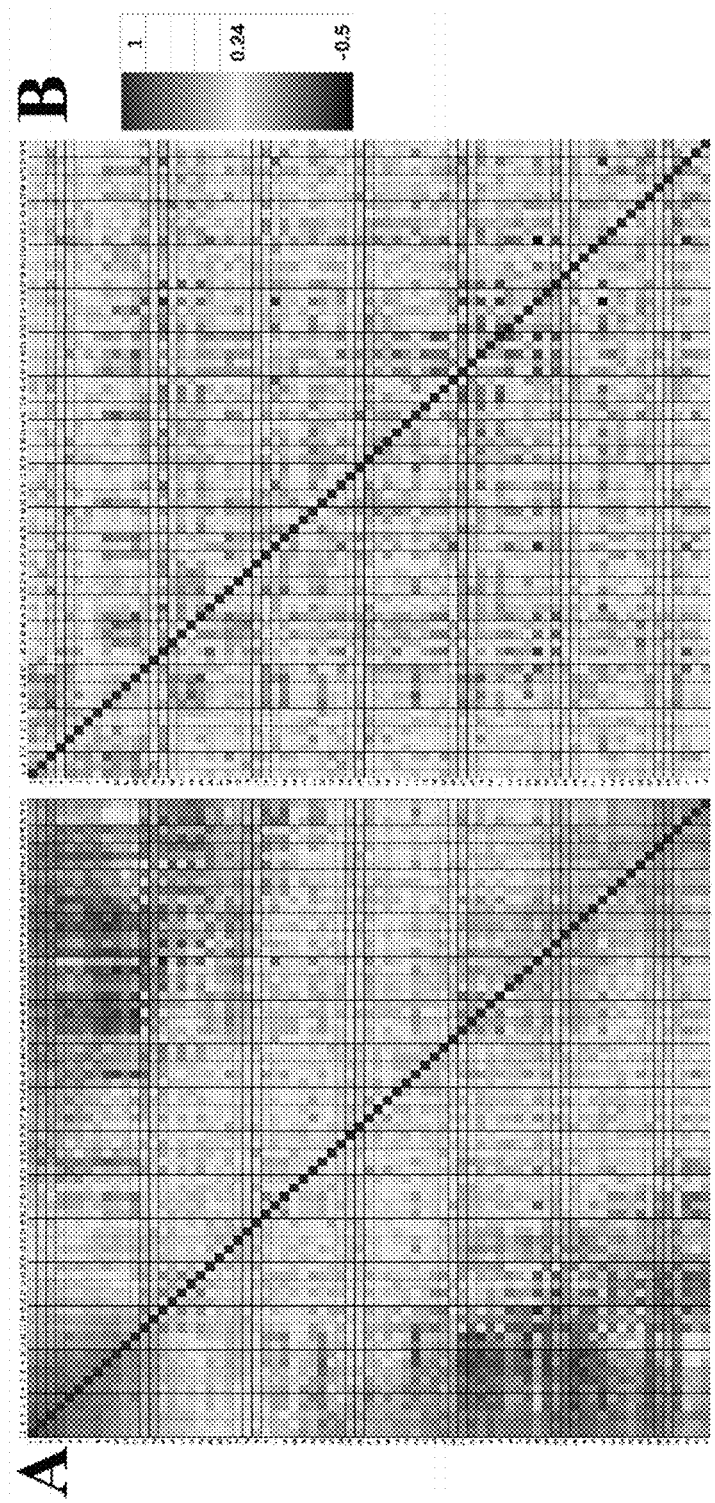
FIG. 1 is a correlation heat map of QC samples before and after correction in a positive ion mode; (A) is a correlation heat map of the QC samples before correction, and (B) is a correlation heat map of the QC samples after correction.

In order to make the objectives, technical solutions and advantages of the examples of the present disclosure more clear, the technical solutions in the examples of the present disclosure are described clearly and completely below. If no specific conditions are specified in the examples, they are carried out under normal conditions or conditions recommended by the manufacturer. If manufacturers of reagents or apparatuses used are not specified, they are conventional products commercially available.

An objective of the present disclosure lies in providing a marker for screening and distinguishing NFC apple juice based on non-targeted metabolomics and use thereof.

The present disclosure is realized as follows:

In one aspect, the present disclosure provides a marker for distinguishing NFC apple juice and FC apple juice, which is at least one selected from the following molecules: gallocatechin, catechin, taxifolin, p-hydroxybenzaldehyde, 5-methoxysalicylic acid, azelaic acid, caffeic acid, chlorogenic acid, epicatechin, eriodictyol, ferulic acid, isoquercitrin, naringenin, n-fructosyl isoleucine, p-coumaraldehyde, p-coumaric acid, phloretin, phlorizin, procyanidin B1, quercetin-3-O-galactoside and rutin.

In the present disclosure, the above markers with differential expression are screened out from NFC apple juice and FC apple juice samples, and upon verification, using these as markers for distinguishing the NFC apple juice and the FC apple juice has good accuracy. The present disclosure provides a novel marker and method of distinguishing the NFC apple juice and the FC apple juice.

It should be noted that the method for distinguishing the NFC apple juice and the FC apple juice using the above markers may be carried out by establishing a distinguishing model, and may also be carried out using a threshold value. Regardless of the method, as long as at least one of the above markers is used to distinguish the NFC apple juice and the FC apple juice, it belongs to the scope of protection of the present disclosure.

The English names and molecular formulas of the above markers are shown in the following table:

| Name of Markers | English Names | Molecular Formula |
| --- | --- | --- |
| gallocatechin | (−)-Gallocatechin | $C_{15}H_{14}O_7$ |
| catechin | (+)-Catechin | $C_{15}H_{14}O_6$ |
| taxifolin | (+−)-Taxifolin | $C_{15}H_{12}O_7$ |
| p-hydroxybenzaldehyde | p-Hydroxybenzaldehyde | $C_7H_6O_2$ |
| 5-methoxysalicylic acid | 5-Methoxysalicylic acid | $C_8H_8O_4$ |
| azelaic acid | Azelaic acid | $C_9H_{16}O_4$ |
| caffeic acid | Caffeic acid | $C_9H_8O_4$ |
| chlorogenic acid | Chlorogenic acid | $C_{16}H_{18}O_9$ |
| epicatechin | (−)-Epicatechin | $C_{15}H_{14}O_6$ |
| eriodictyol | Eriodictyol | $C_{15}H_{12}O_6$ |
| ferulic acid | Ferulic acid | $C_{10}H_{10}O_4$ |
| isoquercitrin | Isoquercitrin | $C_{21}H_{20}O_{12}$ |
| naringenin | Naringenin | $C_{15}H_{12}O_5$ |
| n-fructosyl isoleucine | N-Fructosyl isoleucine | $C_{12}H_{23}NO_7$ |
| p-coumaraldehyde | p-Coumaraldehyde | $C_9H_8O_2$ |
| p-coumaric acid | p-Coumaric acid | $C_9H_8O_3$ |
| phloretin | Phloretin | $C_{15}H_{14}O_5$ |
| phlorizin | Phlorizin | $C_{21}H_{24}O_{10}$ |
| procyanidin B1 | Procyanidin B1 | $C_{30}H_{26}O_{12}$ |
| quercetin-3-O-galactoside | Quercetin-3-O-galactoside | $C_{21}H_{20}O_{12}$ |
| rutin | Rutin | $C_{27}H_{30}O_{16}$ |

In another aspect, the present disclosure provides use of the above marker in distinguishing NFC apple juice and FC apple juice.

Optionally, in some embodiments of the present disclosure, the use includes: detecting a content of the marker in an apple juice sample to be distinguished; and judging whether the apple juice sample to be distinguished is NFC apple juice or FC apple juice according to the content of the marker.

Optionally, in some embodiments of the present disclosure, the judging includes: substituting the obtained content of the apple juice sample to be distinguished into a distinguishing model for distinguishing, wherein the distinguishing model is a PLS-DA model constructed according to the contents of the marker in an NFC apple juice sample and a FC apple juice sample.

Optionally, in some embodiments of the present disclosure, the contents of the marker in the sample to be distinguished, the NFC apple juice sample and the FC apple juice sample are detected by a chromatographic technique, a mass-spectrometric technique or a combination thereof.

The method of detecting the marker content during construction of the distinguishing model is consistent with the method of detecting the marker content in the sample to be distinguished, which can improve the accuracy of the detection result, and avoid misjudgment due to different methods.

Optionally, in some embodiments of the present disclosure, the content of the marker is detected by the chromatographic technique in combination with the mass-spectrometric technique, and the content of the marker is expressed by peak area.

Optionally, in some embodiments of the present disclosure, the number of the NFC apple juice samples and the number of the FC apple juice samples used to construct the PLS-DA model are both greater than or equal to 2.

The number of samples used in establishing the PLS-DA model is more than 2 as much as possible, the more the number is, the higher the accuracy of the distinguishing result of the model can be. A person skilled in the art could rationally determine the number according to practical situations. However, regardless of the number of samples for constructing the model, as long as the above marker content provided in the present disclosure is taken as the basic data for constructing the model, it belongs to the scope of protection of the present disclosure.

Optionally, in some embodiments of the present disclosure, the PLS-DA model is established according to the content data of the marker accumulated in a positive ion mode or a negative ion mode.

Optionally, in some embodiments of the present disclosure, when the PLS-DA model is established in the positive ion mode, parameters are set as follows: the number of principle components is 2, Type I error is 0.01, and outliers' significance is 0.05; and when the PLS-DA model is established in the negative ion mode, parameters are set as follows as follows: the number of principle components is 10, Type I error is 0.01, and the outliers' significance is 0.05.

Optionally, in some embodiments of the present disclosure, the marker used for the PLS-DA model established in the positive ion mode is at least one selected from the following markers: gallocatechin, catechin, p-hydroxybenzaldehyde, caffeic acid, chlorogenic acid, epicatechin, isoquercitrin, n-fructosyl isoleucine, p-coumaric acid, phloretin, phlorizin, procyanidin B1, quercetin-3-O-galactoside and rutin.

It should be noted that, when the PLS-DA model is constructed in the positive ion mode (namely, the PLS-DA model is constructed using the data of the marker in the positive ion mode), the marker used may be any one, any two, any three, any four, any five, any six, any seven, any eight, any nine, any ten, any eleven, any twelve, any thirteen or fourteen of gallocatechin, catechin, p-hydroxybenzaldehyde, caffeic acid, chlorogenic acid, epicatechin, isoquercitrin, n-fructosyl isoleucine, p-coumaric acid, phloretin, phlorizin, procyanidin B1, quercetin-3-O-galactoside and rutin; and all of the models constructed can achieve better discrimination effects.

Optionally, in some embodiments of the present disclosure, the marker used for the PLS-DA model established in the negative ion mode is at least one selected from the following markers: gallocatechin, catechin, taxifolin, p-hydroxybenzaldehyde, 5-methoxysalicylic acid, azelaic acid, caffeic acid, chlorogenic acid, epicatechin, eriodictyol, ferulic acid, isoquercitrin, naringenin, p-coumaraldehyde, p-coumaric acid, phloretin, phlorizin, procyanidin B1, quercetin-3-O-galactoside and rutin.

It should be noted that, when the PLS-DA model is constructed in the negative ion mode, the marker used may be any one, any two, any three, any four, any five, any six, any seven, any eight, any nine, any ten, any eleven, any twelve, any thirteen, any fourteen, any fifteen, any sixteen, any seventeen, any eighteen, any nineteen or twenty of gallocatechin, catechin, taxifolin, p-hydroxybenzaldehyde, 5-methoxysalicylic acid, azelaic acid, caffeic acid, chlorogenic acid, epicatechin, eriodictyol, ferulic acid, isoquercitrin, naringenin, p-coumaraldehyde, p-coumaric acid, phloretin, phlorizin, procyanidin B1, quercetin-3-O-galactoside and rutin; and all of the models constructed can achieve better discrimination effects.

Optionally, in some embodiments of the present disclosure, the PLS-DA model is established by accumulating the content data of the following markers in the positive ion mode: gallocatechin, catechin, p-hydroxybenzaldehyde, caffeic acid, chlorogenic acid, epicatechin, isoquercitrin, n-fructosyl isoleucine, p-coumaric acid, phloretin, phlorizin, procyanidin B1, quercetin-3-O-galactoside and rutin.

Optionally, in some embodiments of the present disclosure, the chromatographic condition used for detecting the content of the marker by the chromatographic technique in combination with the mass-spectrometric technique is as follows:

performing gradient elution with a mobile phase A and a mobile phase B, wherein the mobile phase A is 0.2% aqueous formic acid solution, the mobile phase B is acetonitrile, the flow rate is 300 μL/min, and the feeding volume is 2 μL; and a condition of the gradient elution is as follows:

0-11.50 min, 5%-30% B; 11.50-11.51 min, 30-100% B; 11.51-15.00 min, 100% B; 15.00-15.01 min, 100%-5% B; 15.01-18 min, 5% B; and each numerical parameter may fluctuate in the range of ±5%.

Optionally, in some embodiments of the present disclosure, the mass-spectrometric condition used for detecting the content of the marker by the chromatographic technique in combination with the mass-spectrometric technique is as follows:

in the positive ion mode, the curtain gas is 25, the ion source gas 1 is 50, the ion source gas 2 is 50, the ion source temperature is 500° C., the ion source spray voltage is 5.5 kV, the declustering potential is 60 V, the mass range of the MS1 scan is 100-1000, the collision energy is 10 eV, the mass range of the MS2 scan is 50-1000, the collision energy is 35 eV, and the collision energy spread is 15 eV;

in the negative ion mode, the curtain gas is 25, the ion source gas 1 is 50, the ion source gas 2 is 50, the ion source temperature is 500° C., the ion source spray voltage is −4.5 kV, the declustering potential is −60 V, the mass range of the MS1 scan is 100-1000, the collision energy is −10 eV, the mass range of the MS2 scan is 50-1000, the collision energy is −35 eV, and the collision energy spread is 15 eV; and each numerical parameter may fluctuate in the range of ±5%.

The above-mentioned chromatographic condition and mass-spectrometric condition may better separate the above markers, which is beneficial for realizing accurate measurement of the content of each of the above markers, and further improves the accuracy of the distinguishing result.

Retention time and m/z information of the above markers under the above detection conditions are shown in the following Table 1:

TABLE 1

| Name of Markers | Ion Mode | Adduct Ion Type | Mass-to-charge Ratio (m/z) | Deviation (ppm) | Retention Time (min) |
|---|---|---|---|---|---|
| gallocatechin | positive | M + H | 307.07791 | −10.71 | 3.20 |
| gallocatechin | negative | M − H | 305.06589 | −2.66 | 3.20 |
| catechin | positive | M + H | 291.08575 | −1.89 | 5.19 |
| catechin | negative | M − H | 289.0705 | −4.5 | 5.19 |

TABLE 1-continued

| Name of Markers | Ion Mode | Adduct Ion Type | Mass-to-charge Ratio (m/z) | Deviation (ppm) | Retention Time (min) |
|---|---|---|---|---|---|
| taxifolin | positive | M + H | 305.06267 | −9.6 | 9.14 |
| taxifolin | negative | M − H | 303.04996 | −3.43 | 9.16 |
| p-hydroxybenzaldehyde | positive | M + H | 123.04305 | 9.58 | 6.03 |
| p-hydroxybenzaldehyde | negative | M − H | 121.03066 | −0.85 | 6.03 |
| 5-methoxysalicylic acid | positive | M + H | 169.04945 | −0.3 | 11.19 |
| 5-methoxysalicylic acid | negative | M − H | 167.03789 | 17.3 | 11.20 |
| azelaic acid | positive | M + H | 189.11189 | −1.11 | 10.73 |
| azelaic acid | negative | M − H | 187.09761 | 0.05 | 10.73 |
| caffeic acid | positive | M + H | 181.04892 | −0.32 | 5.95 |
| caffeic acid | negative | M − H | 179.03561 | 3.41 | 5.95 |
| chlorogenic acid | positive | M + H | 355.10172 | −0.19 | 5.25 |
| chlorogenic acid | negative | M − H | 353.0882 | 1.13 | 5.25 |
| epicatechin | positive | M + H | 291.08591 | −1.34 | 6.48 |
| epicatechin | negative | M − H | 289.0718 | −3.56 | 6.47 |
| eriodictyol | positive | M + H | 289.06999 | −2.46 | 12.70 |
| eriodictyol | negative | M − H | 287.05875 | 9.23 | 12.72 |
| ferulic acid | positive | M + H | 195.06492 | −1.44 | 8.77 |
| ferulic acid | negative | M − H | 193.05051 | −0.47 | 8.78 |
| isoquercitrin | positive | M + H | 465.10321 | 0.09 | 9.16 |
| isoquercitrin | negative | M − H | 463.08713 | −2.31 | 9.15 |
| naringenin | positive | M + H | 273.07557 | −0.48 | 12.76 |
| naringenin | negative | M − H | 271.0618 | 2.21 | 12.77 |
| n-fructosyl isoleucine | positive | M + H | 294.15479 | 0.31 | 1.57 |
| n-fructosyl isoleucine | negative | M − H | 292.13982 | −1.3 | 1.57 |
| p-coumaraldehyde | positive | M + H | 149.0583 | −9.39 | 9.45 |
| p-coumaraldehyde | negative | M − H | 147.04588 | 4.62 | 9.43 |
| p-coumaric acid | positive | M + H | 165.05511 | 0.31 | 7.84 |
| p-coumaric acid | negative | M − H | 163.0415 | 8.59 | 7.84 |
| phloretin | positive | M + H | 275.09219 | 0.29 | 12.76 |
| phloretin | negative | M − H | 273.07724 | 1.61 | 12.77 |
| phlorizin | positive | M + H | 437.14395 | −0.57 | 11.21 |
| phlorizin | negative | M − H | 435.12631 | −7.79 | 11.2 |
| procyanidin B1 | positive | M + H | 579.1496 | −0.17 | 4.48 |
| procyanidin B1 | negative | M − H | 577.13354 | −2.70 | 4.48 |
| quercetin-3-O-galactoside | positive | M + H | 465.10339 | 0.13 | 8.98 |
| quercetin-3-O-galactoside | negative | M − H | 463.08585 | −5.07 | 8.97 |
| rutin | positive | M + H | 611.16156 | 1.41 | 8.78 |
| rutin | negative | M − H | 609.146 | −0.16 | 8.77 |

Optionally, in some embodiments of the present disclosure, the markers include: gallocatechin, catechin, taxifolin, p-hydroxybenzaldehyde, 5-methoxysalicylic acid, azelaic acid, caffeic acid, chlorogenic acid, epicatechin, eriodictyol, ferulic acid, isoquercitrin, naringenin, n-fructosyl isoleucine, p-coumaraldehyde, p-coumaric acid, phloretin, phlorizin, procyanidin B1, quercetin-3-O-galactoside and rutin.

A method for distinguishing NFC apple juice and FC apple juice, wherein the method comprises:
detecting a content of the marker according to claim 1 in an apple juice sample to be distinguished; and judging whether the apple juice sample to be distinguished is NFC apple juice or FC apple juice according to the content of the marker.

Optionally, in some embodiments of the present disclosure, the judging comprises: substituting an obtained content of the apple juice sample to be distinguished into a distinguishing model for distinguishing, wherein the distinguishing model is a PLS-DA model constructed according to contents of the marker in an NFC apple juice sample and a FC apple juice sample.

Optionally, in some embodiments of the present disclosure, contents of the marker in the sample to be distinguished, the NFC apple juice sample and the FC apple juice sample are detected by a chromatographic technique, a mass-spectrometric technique or a combination thereof.

Optionally, in some embodiments of the present disclosure, the content of the marker is detected by the chromatographic technique in combination with the mass-spectrometric technique, and the content of the marker is expressed by a peak area.

Optionally, in some embodiments of the present disclosure, the NFC apple juice sample and the FC apple juice sample used to construct the PLS-DA model are both in a number greater than or equal to 2,
preferably, the PLS-DA model is established according to content data of the marker accumulated in a positive ion mode or a negative ion mode,
preferably, when the PLS-DA model is established in the positive ion mode, parameters are set as follows: principle components are in a number of 2, Type I error is 0.01, and outliers' significance is 0.05; and when the PLS-DA model is established in the negative ion mode, parameters are set as follows: principle components are in a number of 10, Type I error is 0.01, and the outliers' significance is 0.05;
preferably, the marker used for the PLS-DA model established in the positive ion mode is at least one selected from following markers: gallocatechin, catechin, p-hydroxybenzaldehyde, caffeic acid, chlorogenic acid, epicatechin, isoquercitrin, n-fructosyl isoleucine, p-coumaric acid, phloretin, phlorizin, procyanidin B1, quercetin-3-O-galactoside and rutin;

the marker used for the PLS-DA model established in the negative ion mode is at least one selected from following markers: gallocatechin, catechin, taxifolin, p-hydroxybenzaldehyde, 5-methoxysalicylic acid, azelaic acid, caffeic acid, chlorogenic acid, epicatechin, eriodictyol, ferulic acid, isoquercitrin, naringenin, p-coumaraldehyde, p-coumaric acid, phloretin, phlorizin, procyanidin B1, quercetin-3-O-galactoside and rutin; and preferably, the PLS-DA model is established by accumulating content data of the following markers in the positive ion mode: gallocatechin, catechin, p-hydroxybenzaldehyde, caffeic acid, chlorogenic acid, epicatechin, isoquercitrin, n-fructosyl isoleucine, p-coumaric acid, phloretin, phlorizin, procyanidin B1, quercetin-3-O-galactoside and rutin.

Optionally, in some embodiments of the present disclosure, a chromatographic condition used for detecting the content of the marker by the chromatographic technique in combination with the mass-spectrometric technique is as follows:

performing gradient elution with a mobile phase A and a mobile phase B, wherein the mobile phase A is 0.2% aqueous formic acid solution, the mobile phase B is acetonitrile, with a flow rate of 300 μL/min, and a feeding volume of 2 μL, wherein a condition of the gradient elution is as follows: 0-11.50 min, 5%-30% B; 11.50-11.51 min, 30-100% B; 11.51-15.00 min, 100% B; 15.00-15.01 min, 100%-5% B; 15.01-18 min, 5% B, wherein each numerical parameter fluctuates in a range of ±5%.

Optionally, in some embodiments of the present disclosure, a mass-spectrometric condition used for detecting the content of the marker by the chromatographic technique in combination with the mass-spectrometric technique is as follows:

in the positive ion mode, a curtain gas is 25, an ion source gas 1 is 50, an ion source gas 2 is 50, an ion source temperature is 500° C., an ion source spray voltage is 5.5 kV, a declustering potential is 60 V, a mass range of an MS1 scan is 100-1000, a collision energy is 10 eV, a mass range of an MS2 scan is 50-1000, a collision energy is 35 eV, and a collision energy spread is 15 eV; and in the negative ion mode, a curtain gas is 25, an ion source gas 1 is 50, an ion source gas 2 is 50, an ion source temperature is 500° C., an ion source spray voltage is −4.5 kV, a declustering potential is −60 V, a mass range of the MS1 scan is 100-1000, a collision energy is −10 eV, a mass range of the MS2 scan is 50-1000, a collision energy is −35 eV, and a collision energy spread is 15 eV, wherein each numerical parameter fluctuates in a range of ±5%.

Optionally, in some embodiments of the present disclosure, the marker comprises: gallocatechin, catechin, taxifolin, p-hydroxybenzaldehyde, 5-methoxysalicylic acid, azelaic acid, caffeic acid, chlorogenic acid, epicatechin, eriodictyol, ferulic acid, isoquercitrin, naringenin, n-fructosyl isoleucine, p-coumaraldehyde, p-coumaric acid, phloretin, phlorizin, procyanidin B1, quercetin-3-O-galactoside and rutin.

Compared with the distinguishing effect of a single marker, the result of distinguishing using the distinguishing model constructed with a plurality of markers in combination is more accurate.

The features and performances of the present disclosure are further described below in detail in combination with examples.

Example 1

Screening and Verification of Markers for Distinguishing NFC Apple Juice and FC Apple Juice 1. Accumulation and Preparation of Samples NFC apple juice and concentrated apple juice samples were accumulated from typical regions such as Shanxi and Shandong in China, the sources include one plant in Shandong (denoted as Group A) and three plants in Shanxi (denoted as Groups B, C, and D), and varieties, places of origin, batches, sterilization modes (pasteurization and ultra-high pressure non-thermal sterilization) and the like were comprehensively taken into consideration; the number of each kind of apple juice sample from each plant was not less than 18. The NFC apple juice samples included pasteurized apple juice and ultra-high pressure sterilized apple juice. In the above, the pasteurized NFC apple juice of Group A was directly provided by the plant, and the pasteurized NFC apple juice of Groups B, C and D was prepared upon treatment in laboratory at 85° C. for 15 seconds. The ultra-high pressure sterilized NFC apple juice of Groups A, B, C and D was prepared upon treatment under a pressure of 550 MPa for 5 minutes by CQC-30 equipment of Suyuanzhongtian. The concentrated apple juice of Groups A, B, C and D were directly supplied by the plants and reduced to the corresponding sugar degree of each group of NFC apple juice by adding water in laboratory. 270 apple juice samples (180 NFC samples and 90 FC samples) were prepared in total.

Each apple juice sample was centrifuged in a centrifuge (26916 g, 4° C.) for 15 min, then the supernatant was taken and filtered on a PES membrane filter head of 0.45 and 0.22 μm, and then loaded into a sample bottle as a sample for subsequent analysis.

2. Data Accumulation 1) accumulating two sets of data using a liquid chromatography in combination with high-resolution mass spectrometer;

2) performing operations such as peak extraction and deconvolution on the data to obtain a peak table;

3) correcting the QC samples uniformly distributed in an accumulation sequence so as to eliminate in-group batch processing effect;

4) analyzing a detection result using multivariate statistics and a single variable analysis method;

5) performing significant differential analysis on the analysis result to obtain a differential factor between the FC apple juice and the NFC apple juice;

6) comparing the differential factor with a database to obtain a marker; and 7) an accumulation mode may be a data-dependent or non-dependent accumulation mode.

2. Screening and verification of markers that can effectively distinguish NFC apple juice and FC apple juice 1) Accumulating data using an ultra-high performance liquid chromatography in combination with quadrupole time-of-flight high-resolution mass spectrometer Specific parameters of the chromatography system were as follows: all samples were analyzed using an ExionLC ultra-high performance reversed phase liquid chromatography system (SCIEX, Redwood City, CA, USA), mobile phase A was 0.2% aqueous formic acid solution, B was acetonitrile, and the flow rate was 300 μL/min; a feeding volume was 2 μL; a chromatographic column was HSST3 (ACQUITYUPLC, 1.8 μm, 2.1*100 mm, Waters, USA), and a column temperature was kept at 40° C.; and a mobile phase gradient was as follows:

0-11.50 min, 5%-30% B; 11.50-11.51 min, 30-100% B; 11.51-15.00 min, 100% B; 15.00-15.01 min, 100%-5% B; 15.01-18 min, 5% B.

Specific parameters of a mass spectroscopy system were as follows: the mass spectroscopy analysis was performed using a quadrupole time-of-flight (QTOF) high-resolution mass spectrometer (TripleTOF6600, SCIEX, Redwood City, CA, USA), and the TOF MS and MS2 of each sample were scanned in a mode of accumulating all theoretical fragment ions (SWATH) simultaneously from consecutive windows, and each accumulation cycle included 15 SWATH windows. The instrument was calibrated automatically by a calibration delivery system (CDS) (SCIEX, Redwood City, CA, USA) every 4 samples.

Figures 1, 7:
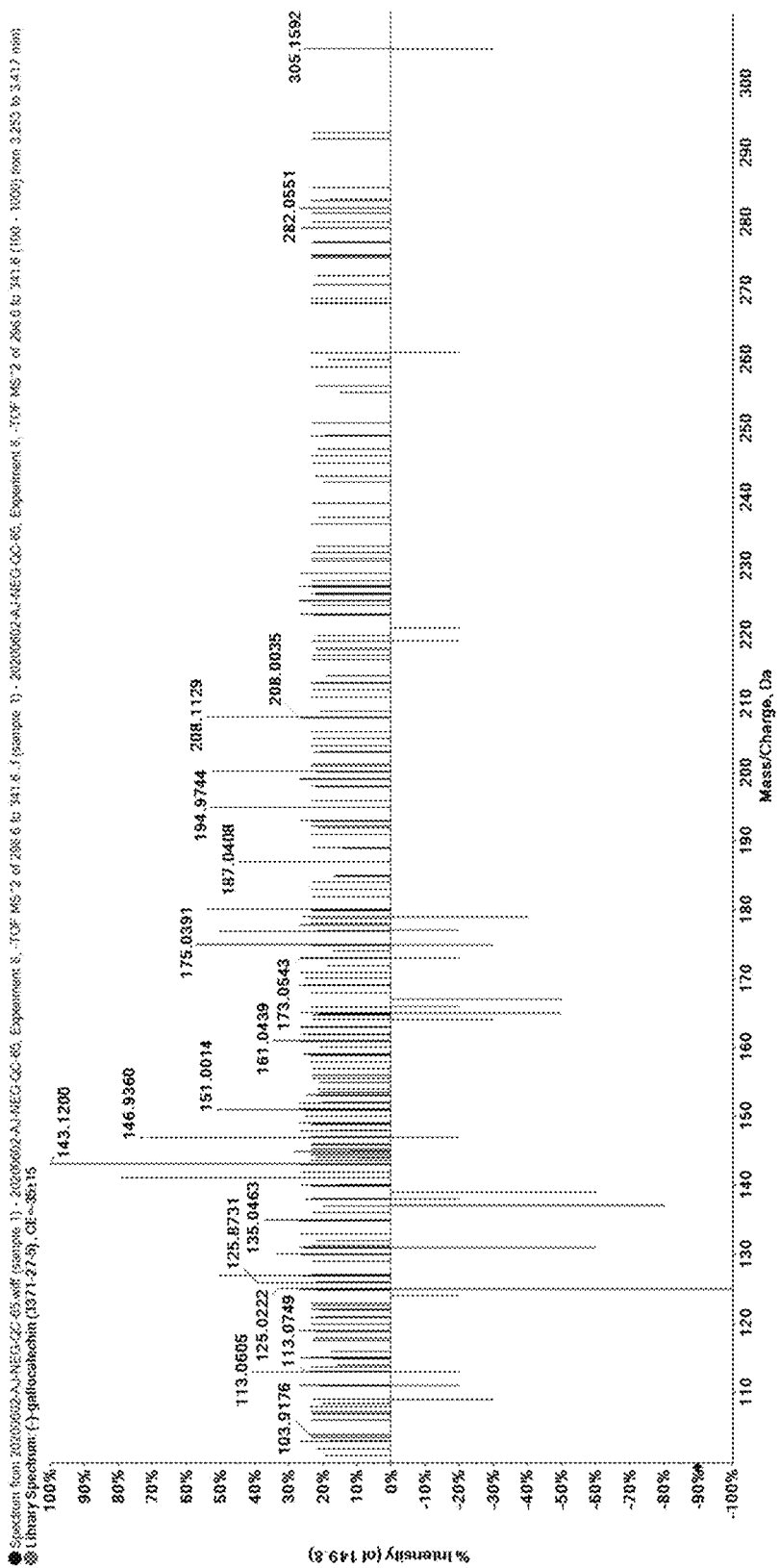
Figures 2, 7:
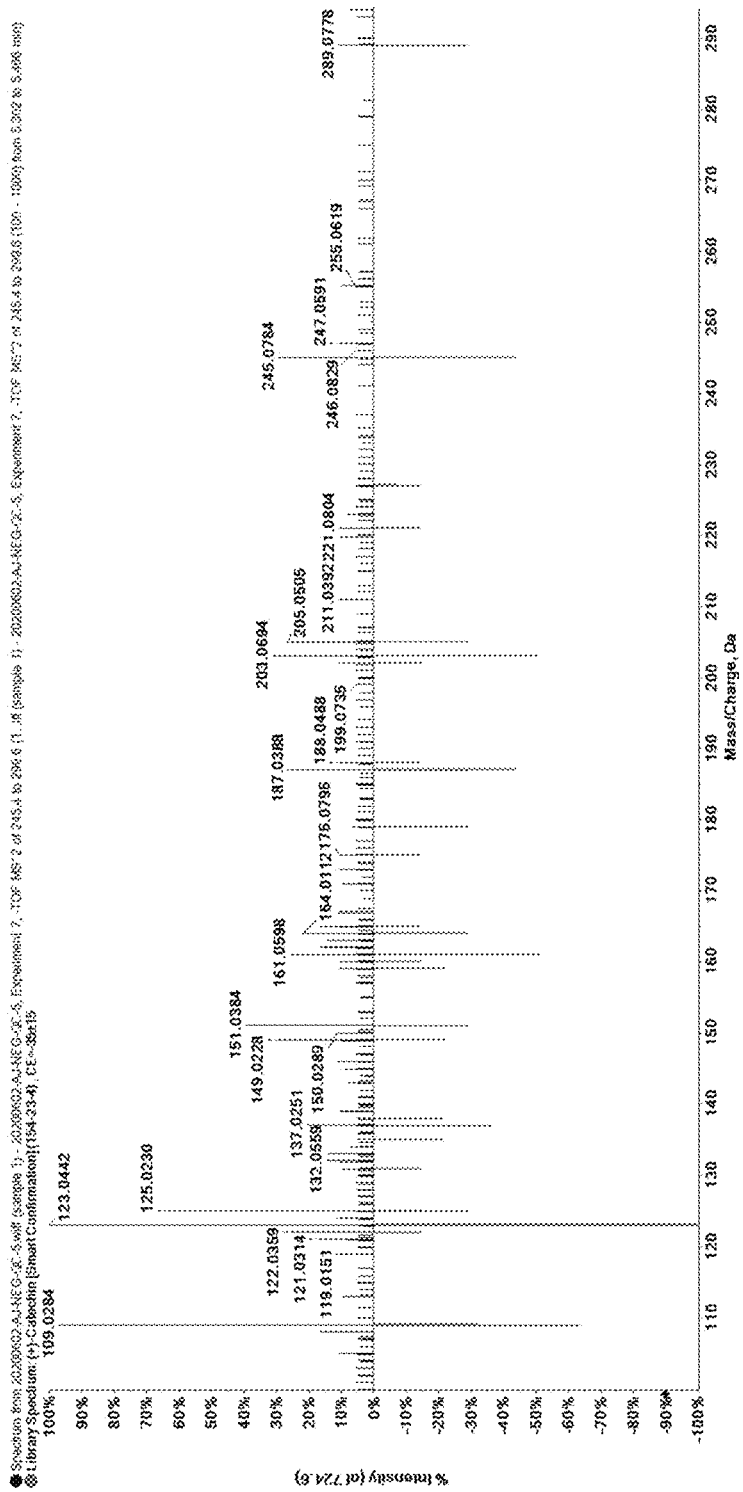
Figures 3, 7:
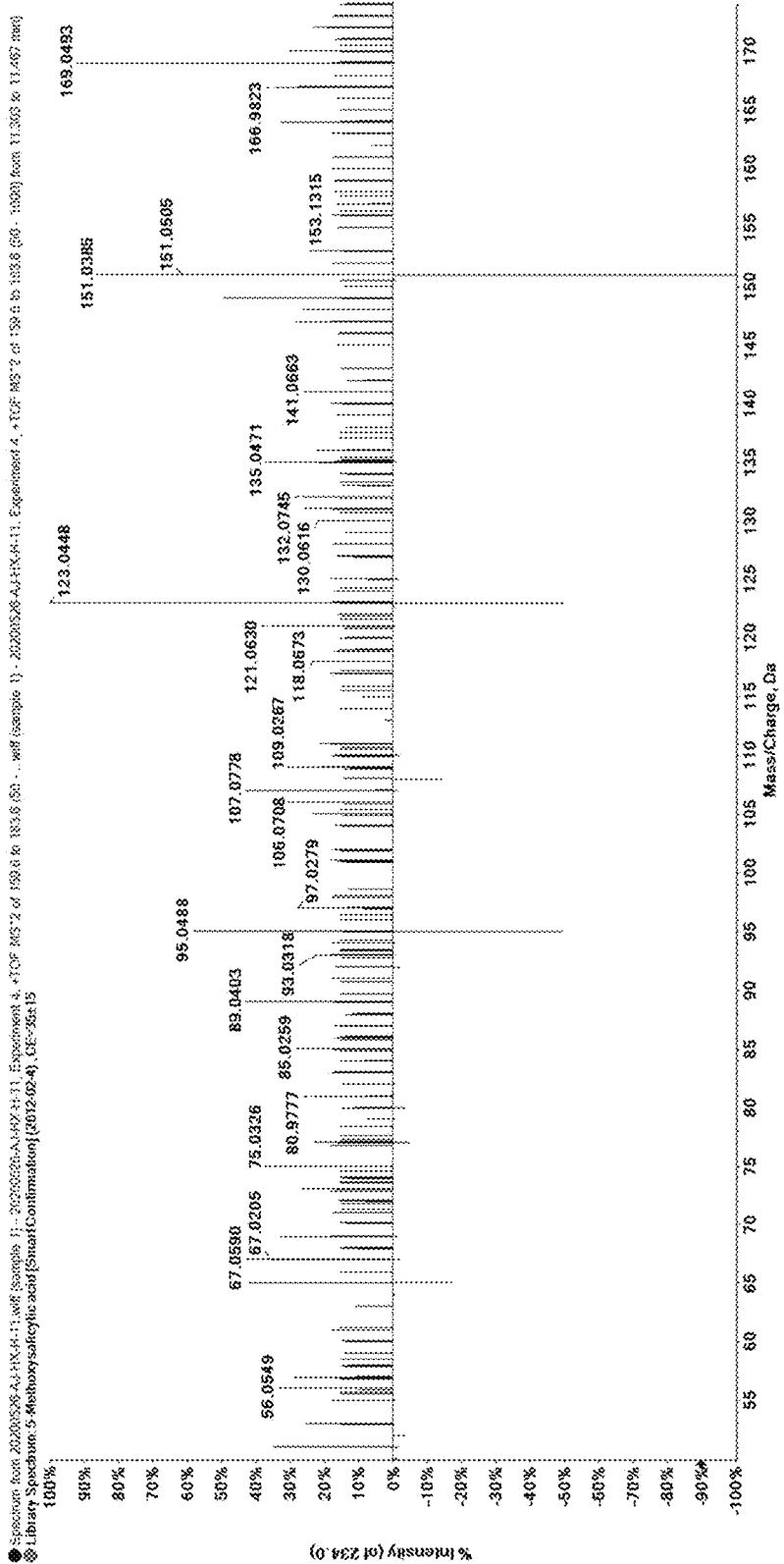
Figures 4, 7:
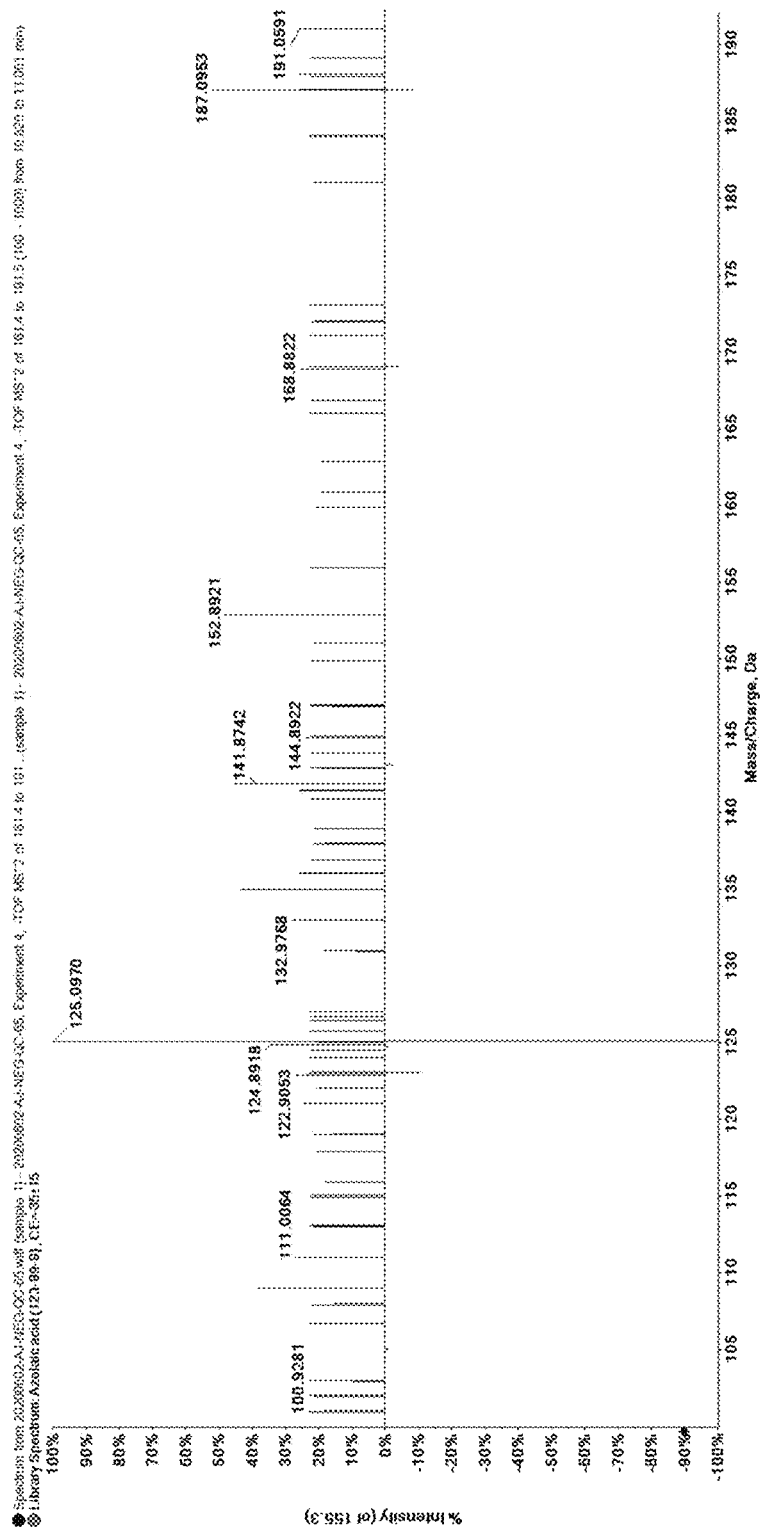
Figures 5, 7:
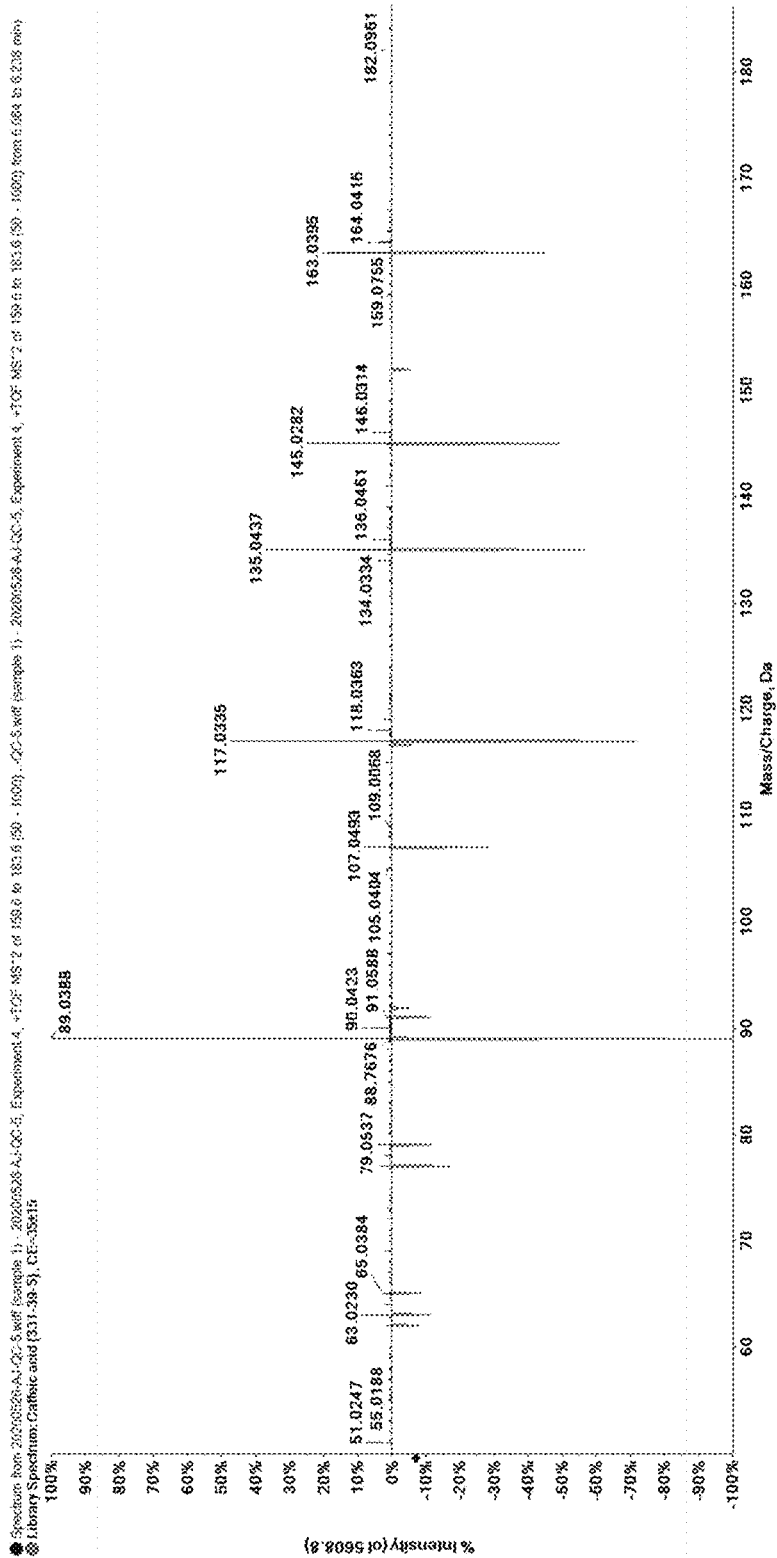
Figures 6, 7:
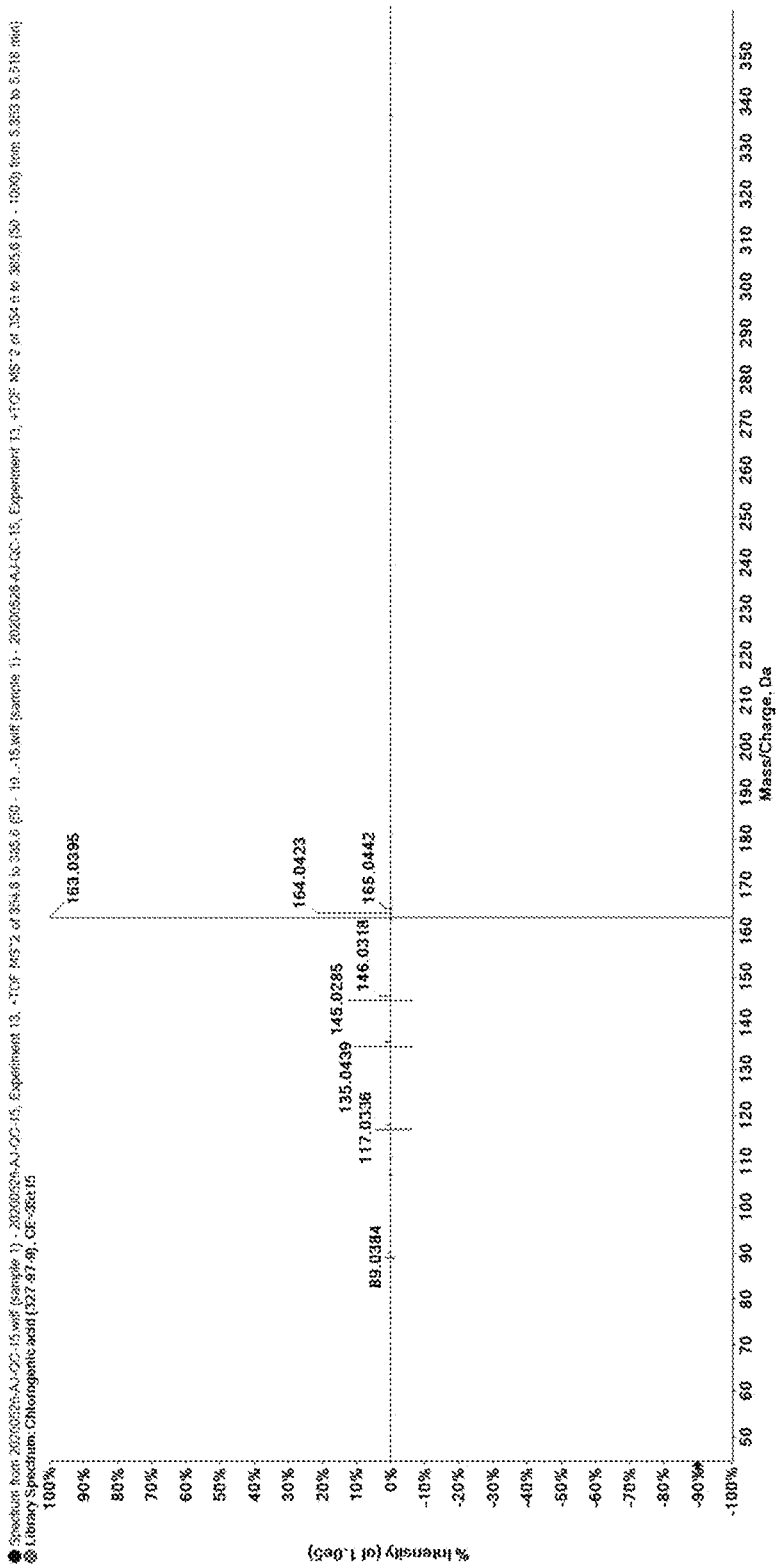
Figure 7:
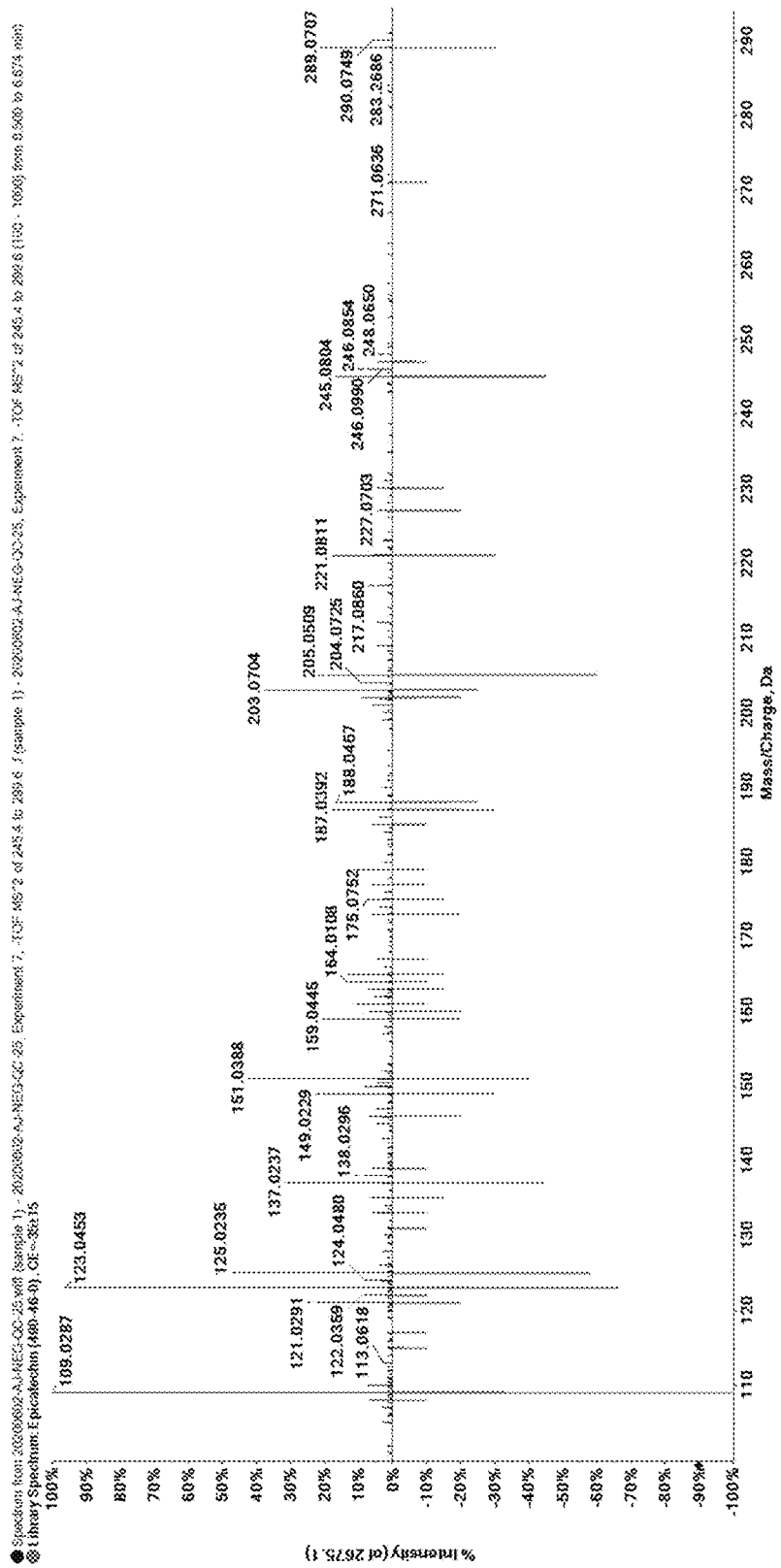
Figures 7, 8:
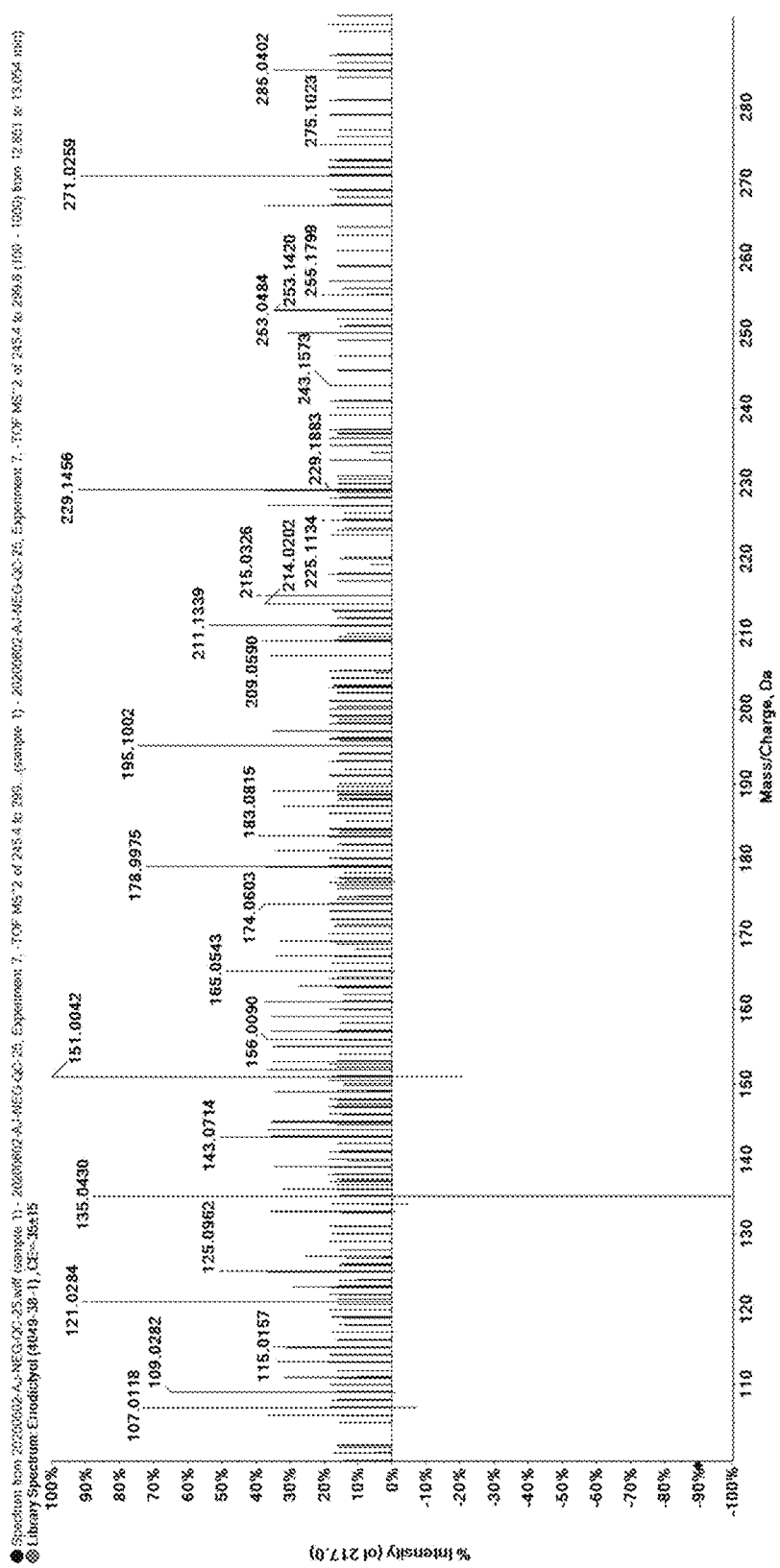
Figures 7, 8, 9:
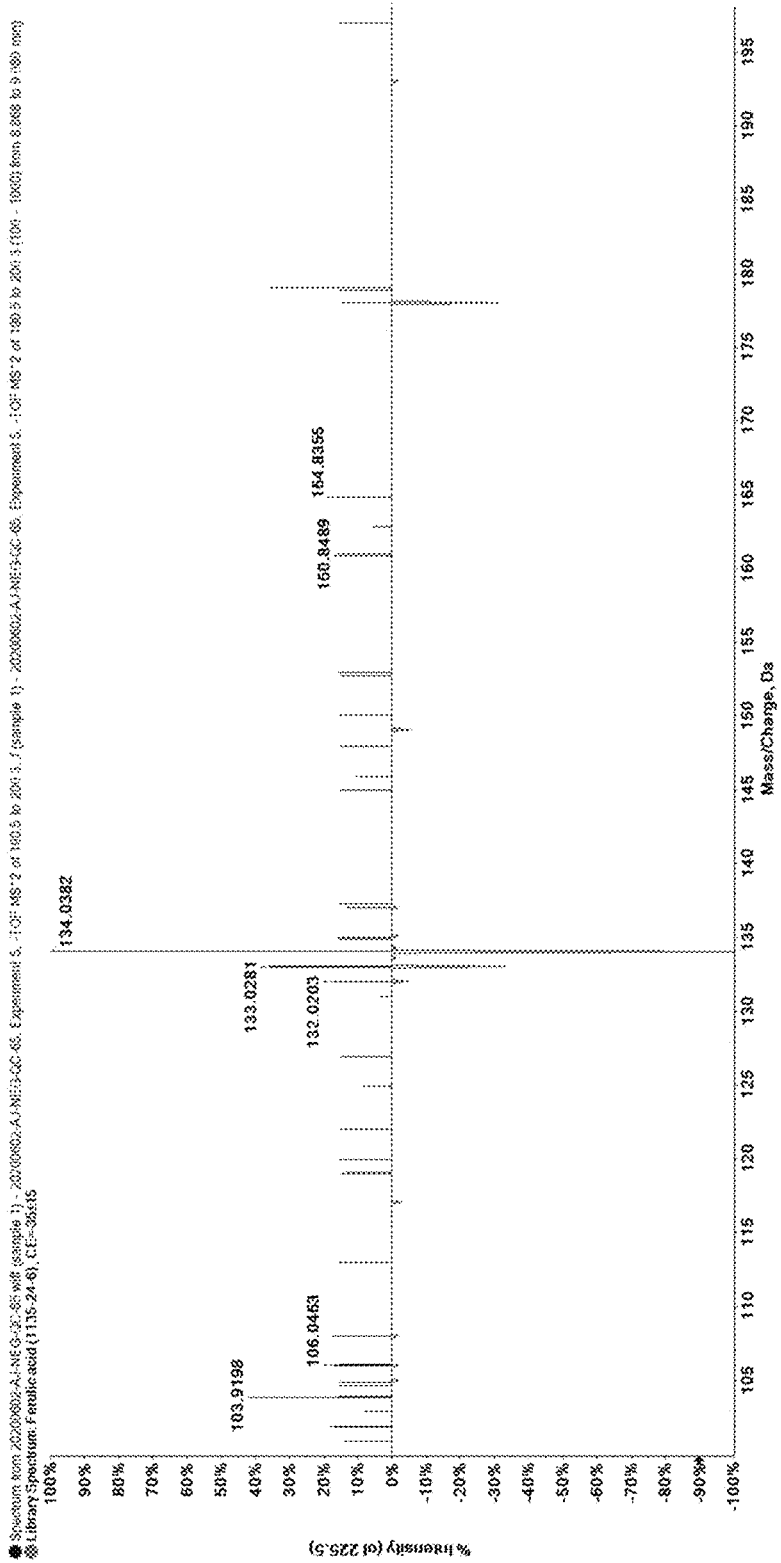
Figures 7, 8, 9, 10:
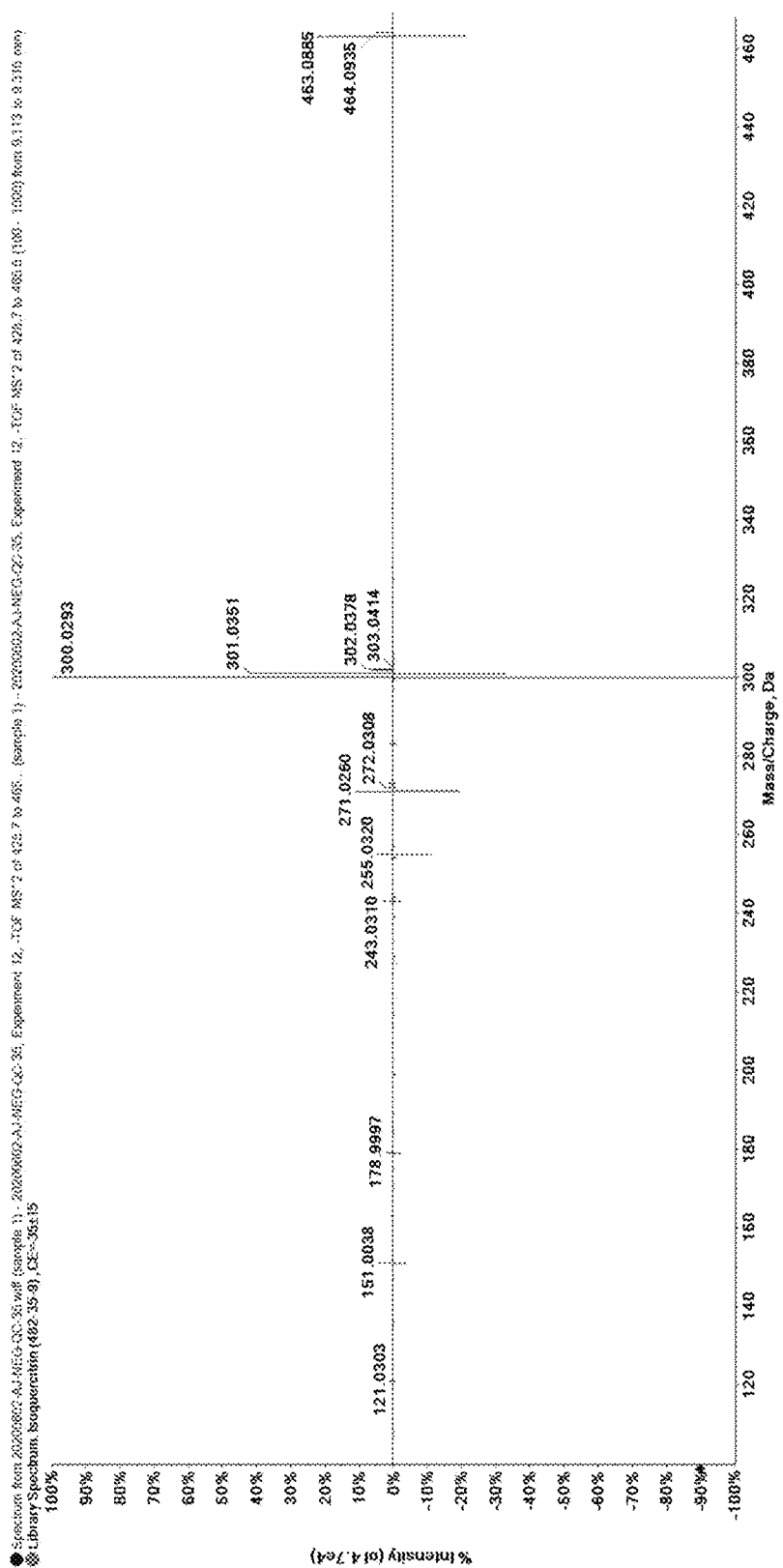
Figures 7, 8, 9, 10, 11:
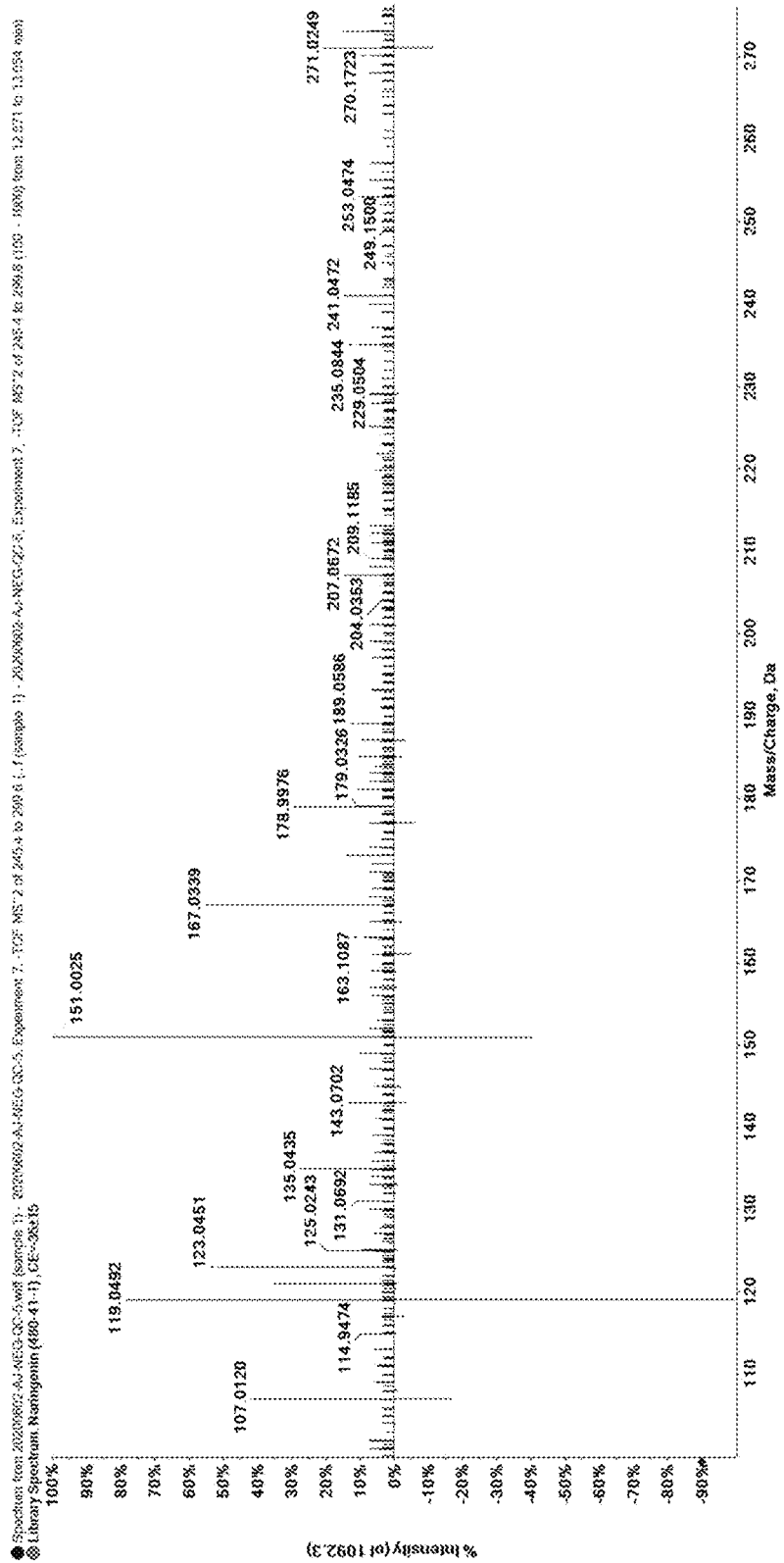
Figures 7, 8, 9, 10, 11, 12:
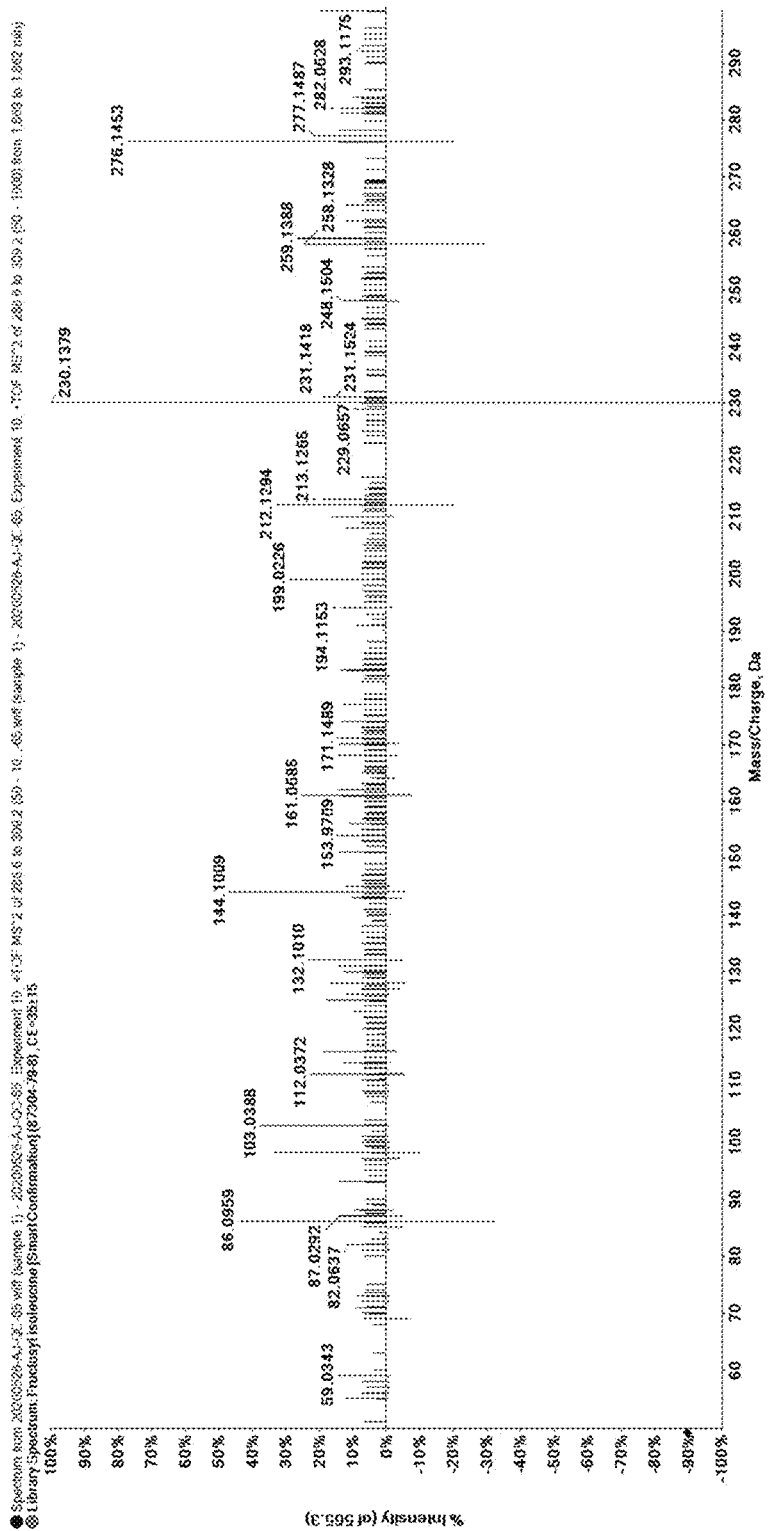
Figures 7, 8, 9, 10, 11, 12, 13:
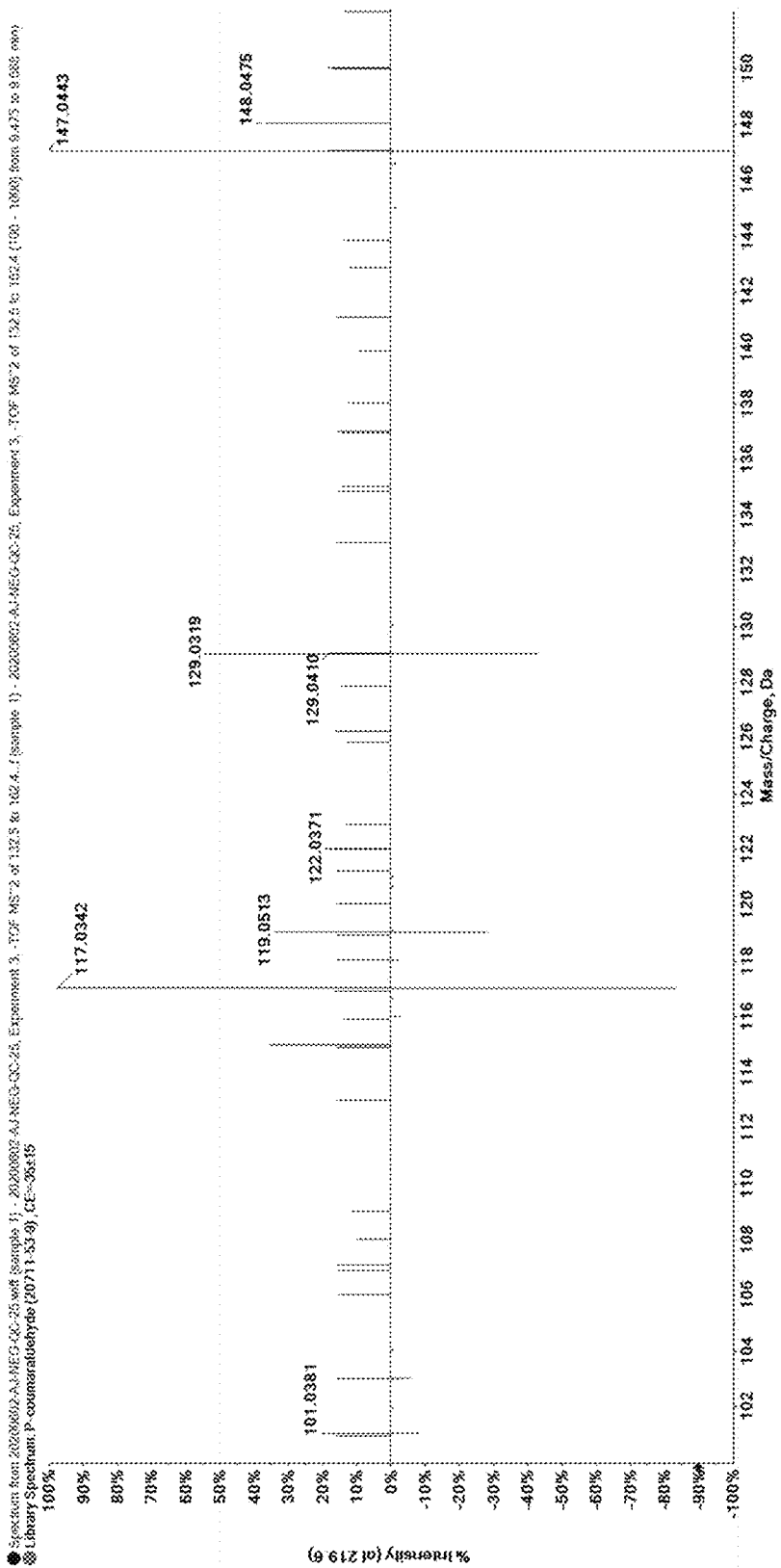
Figures 7, 8, 9, 10, 11, 12, 13, 14:
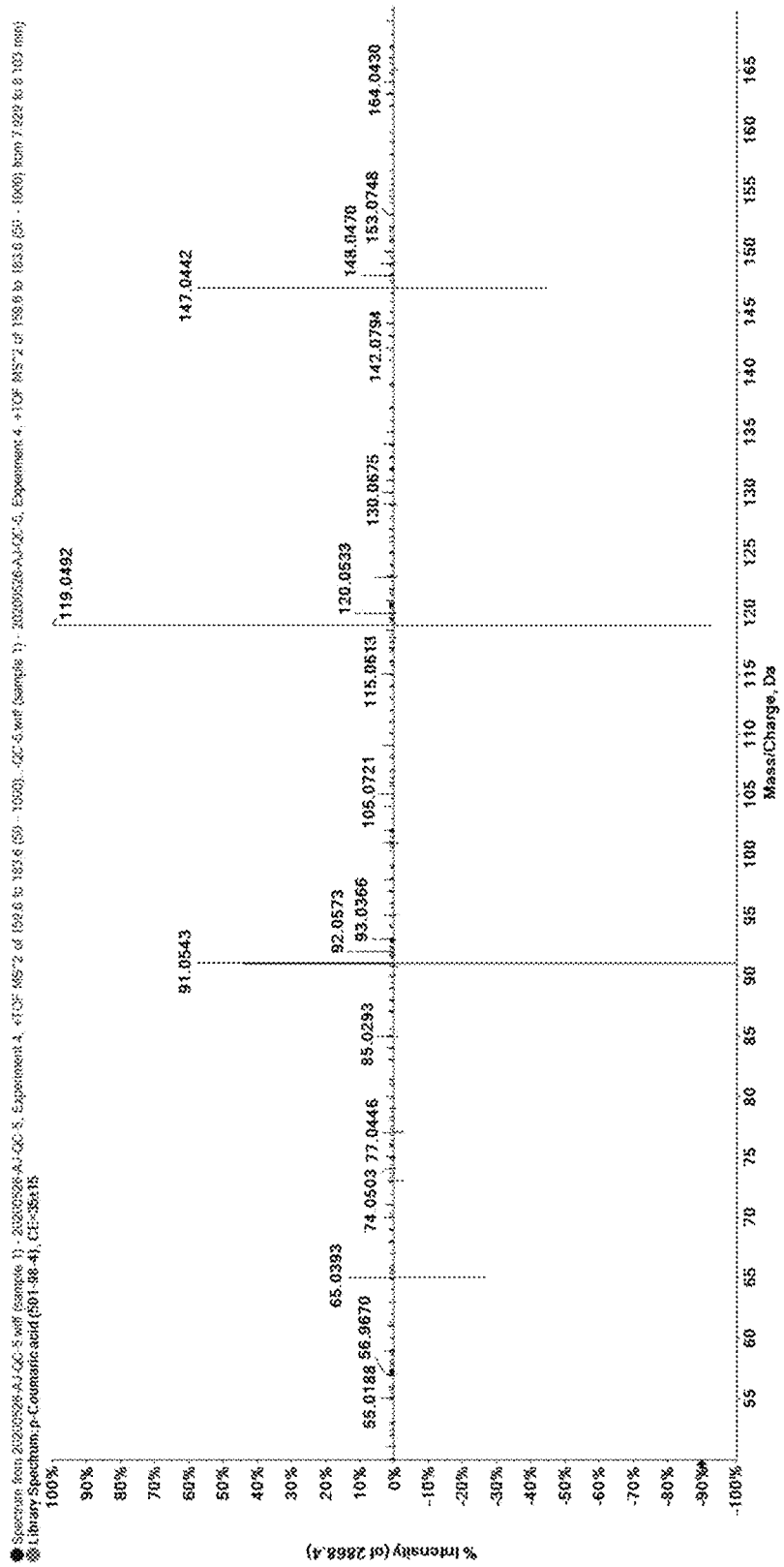
Figures 7, 8, 9, 10, 11, 12, 13, 14, 15:
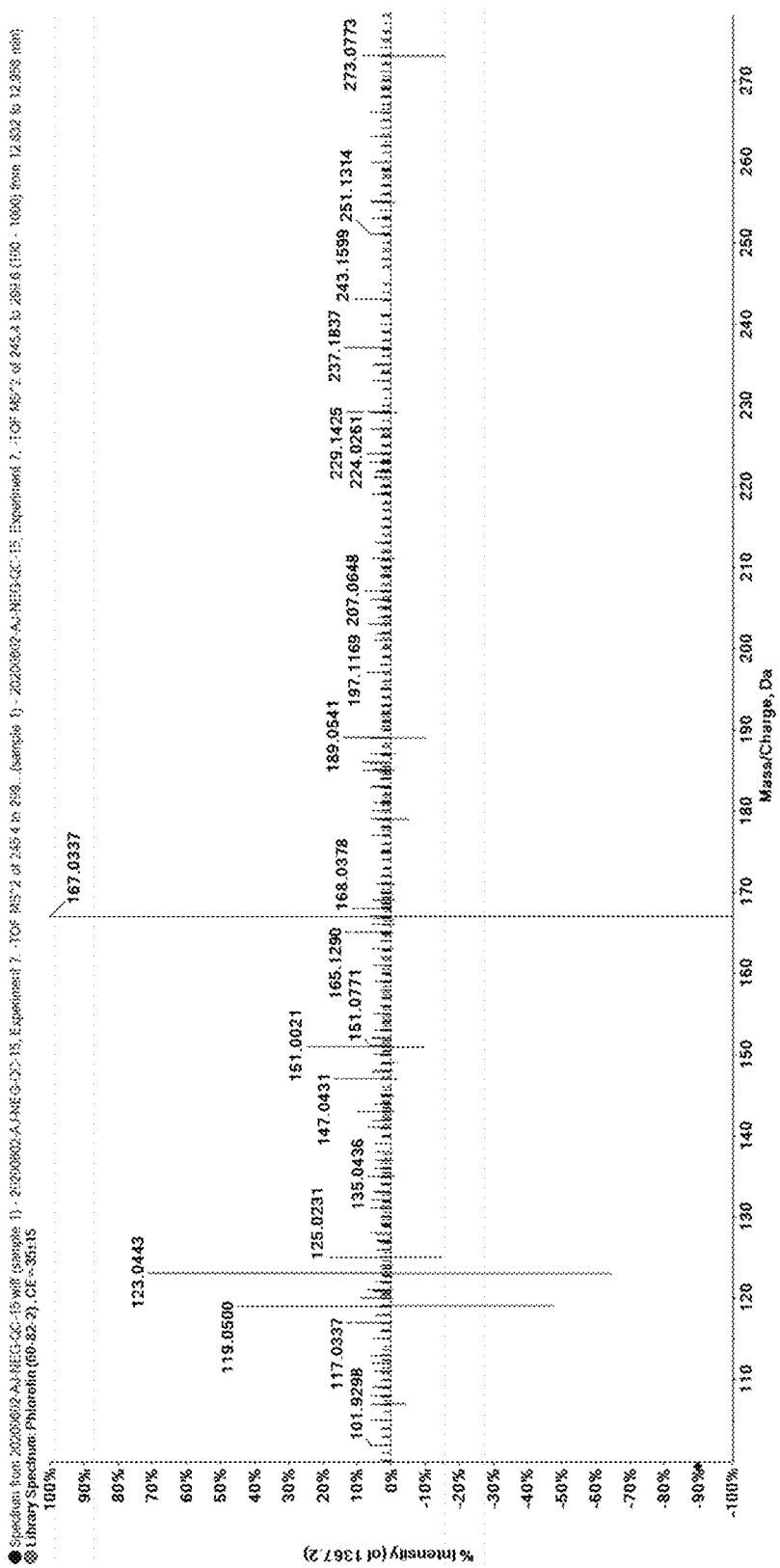
Figures 7, 8, 9, 10, 11, 12, 13, 14, 15, 16:
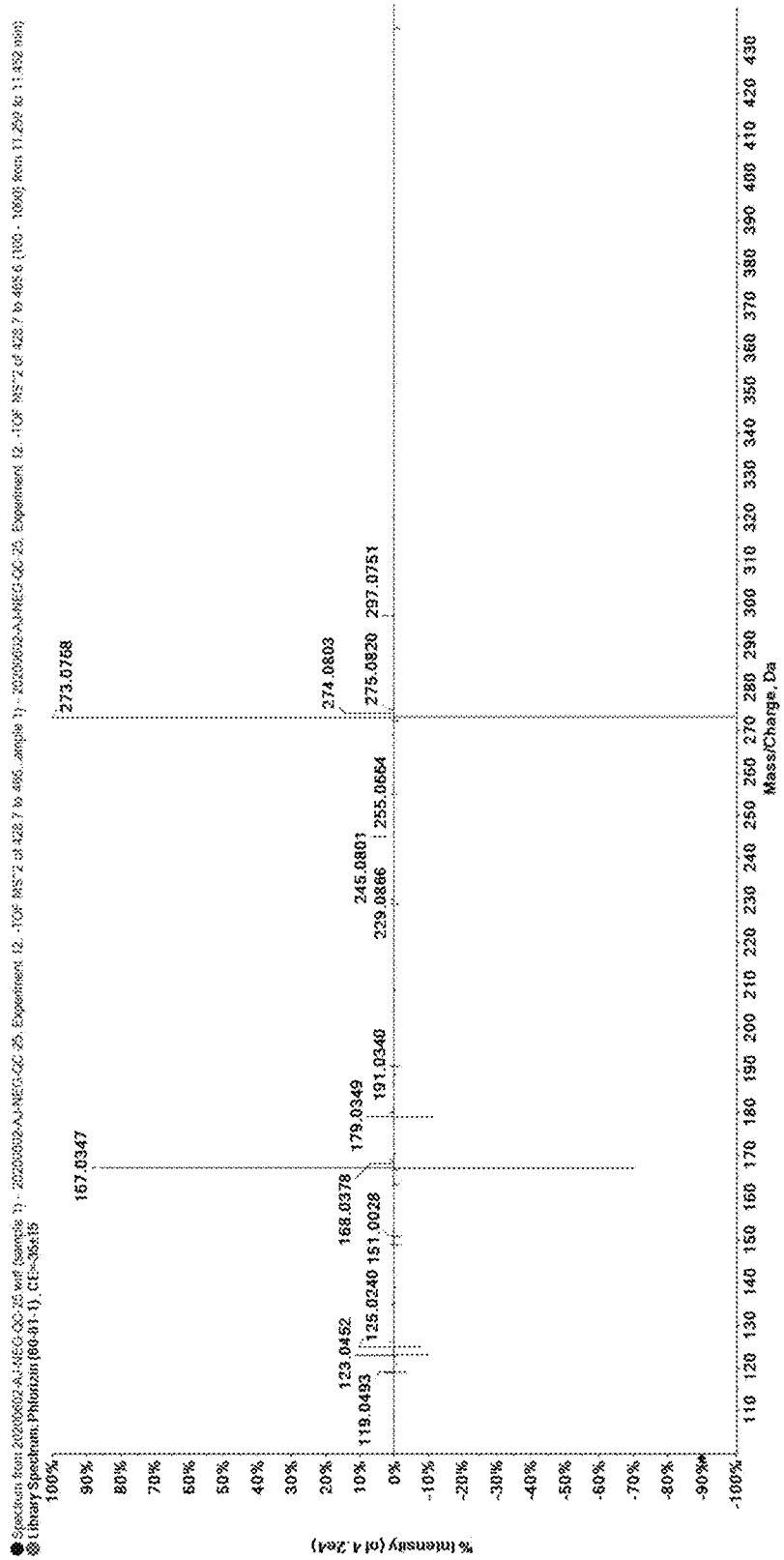
Figures 7, 8, 9, 10, 11, 12, 13, 14, 15, 16, 17:
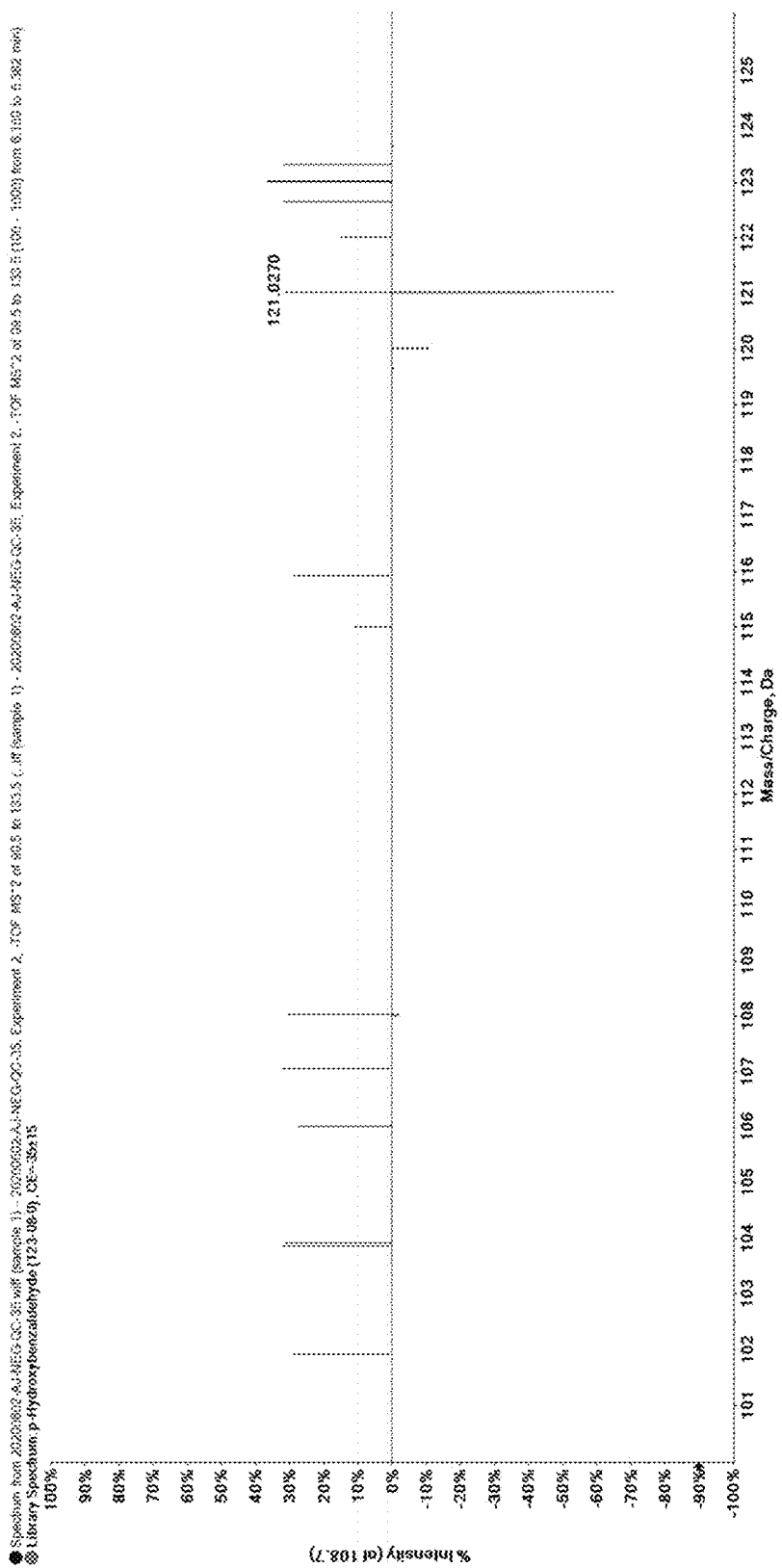
Figures 7, 8, 9, 10, 11, 12, 13, 14, 15, 16, 17, 18:
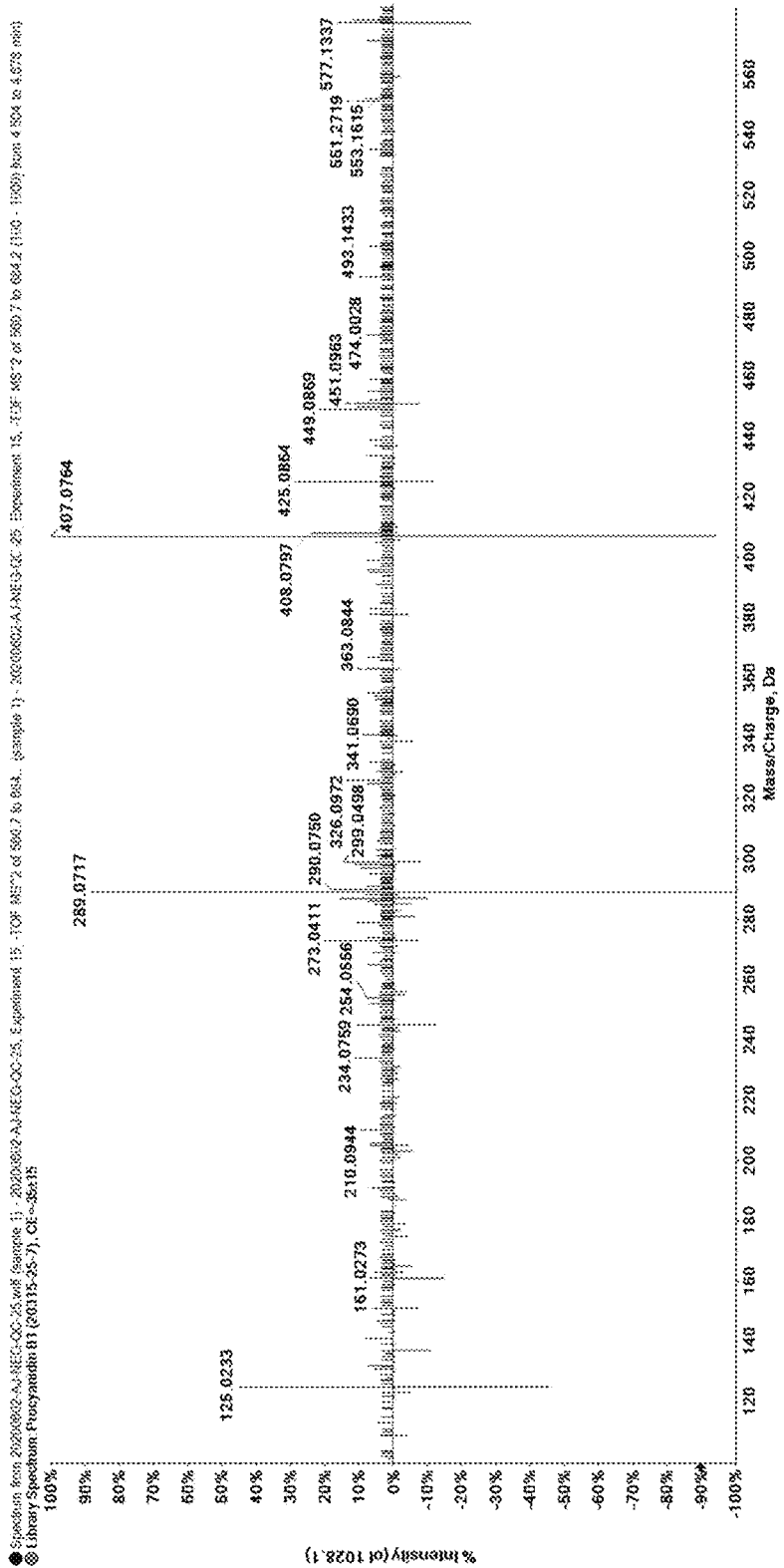
Figures 7, 8, 9, 10, 11, 12, 13, 14, 15, 16, 17, 18, 19:
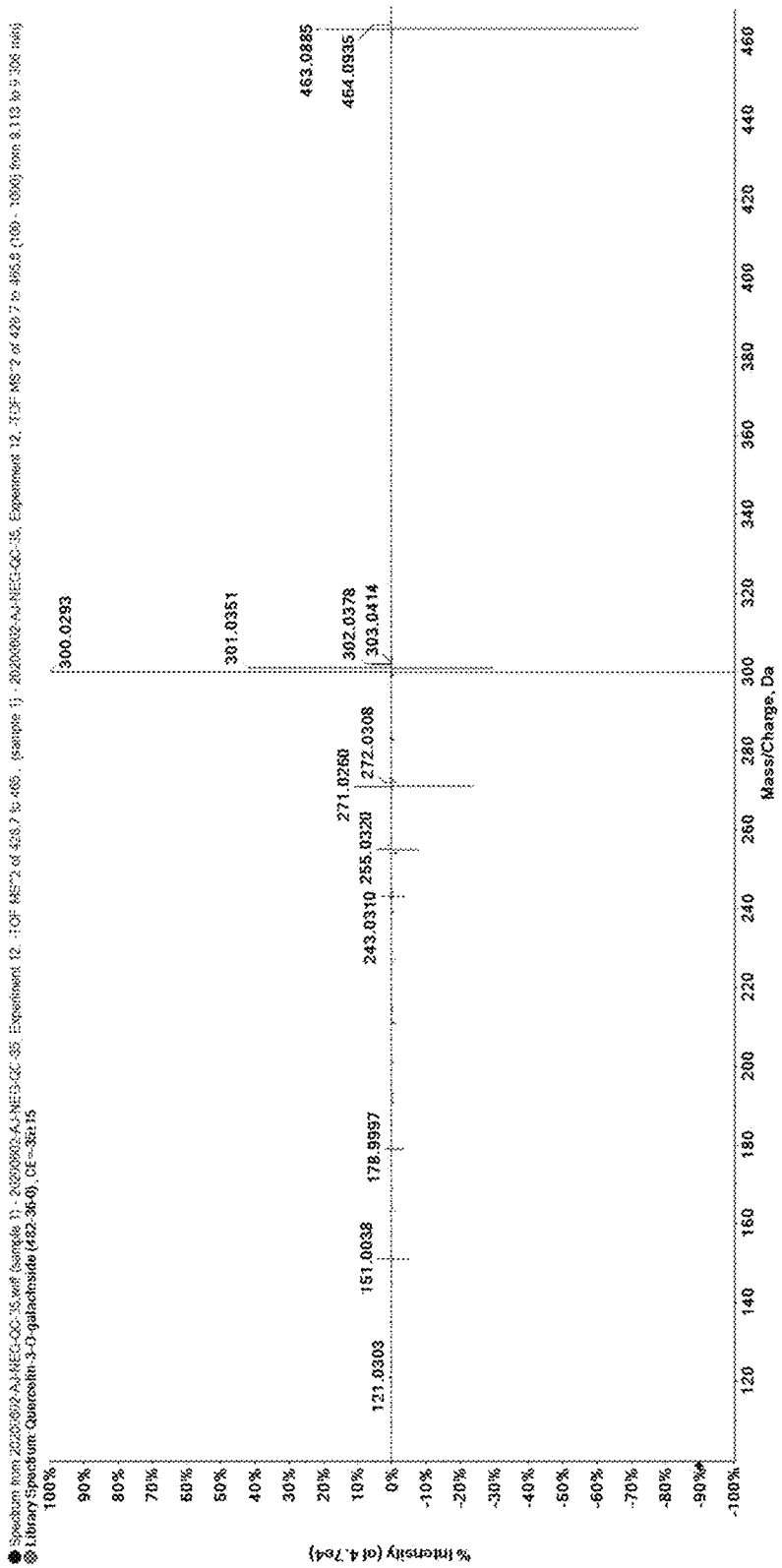
Figures 7, 8, 9, 10, 11, 12, 13, 14, 15, 16, 17, 18, 19, 20:
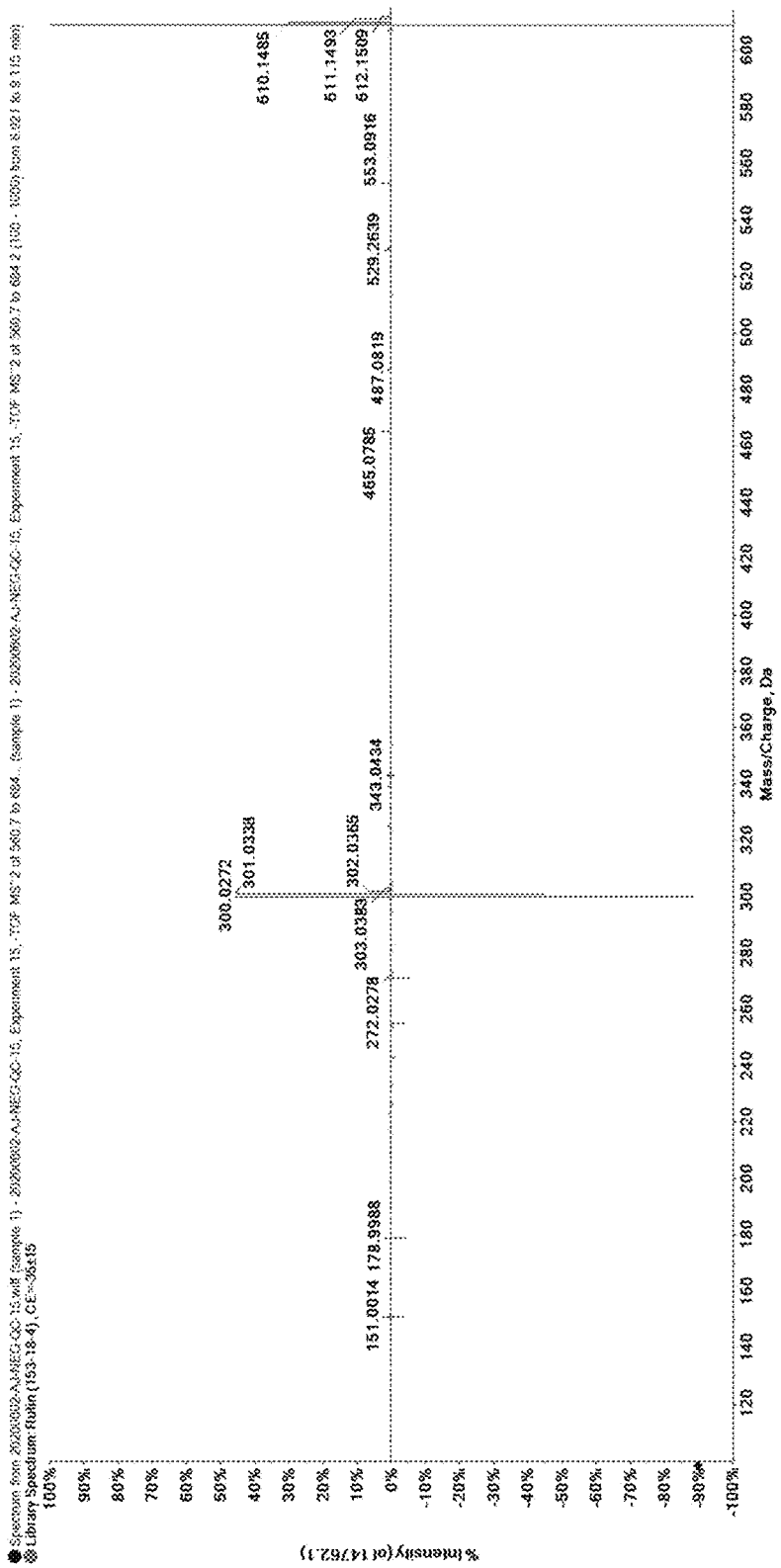
Figures 7, 8, 9, 10, 11, 12, 13, 14, 15, 16, 17, 18, 19, 20, 21:
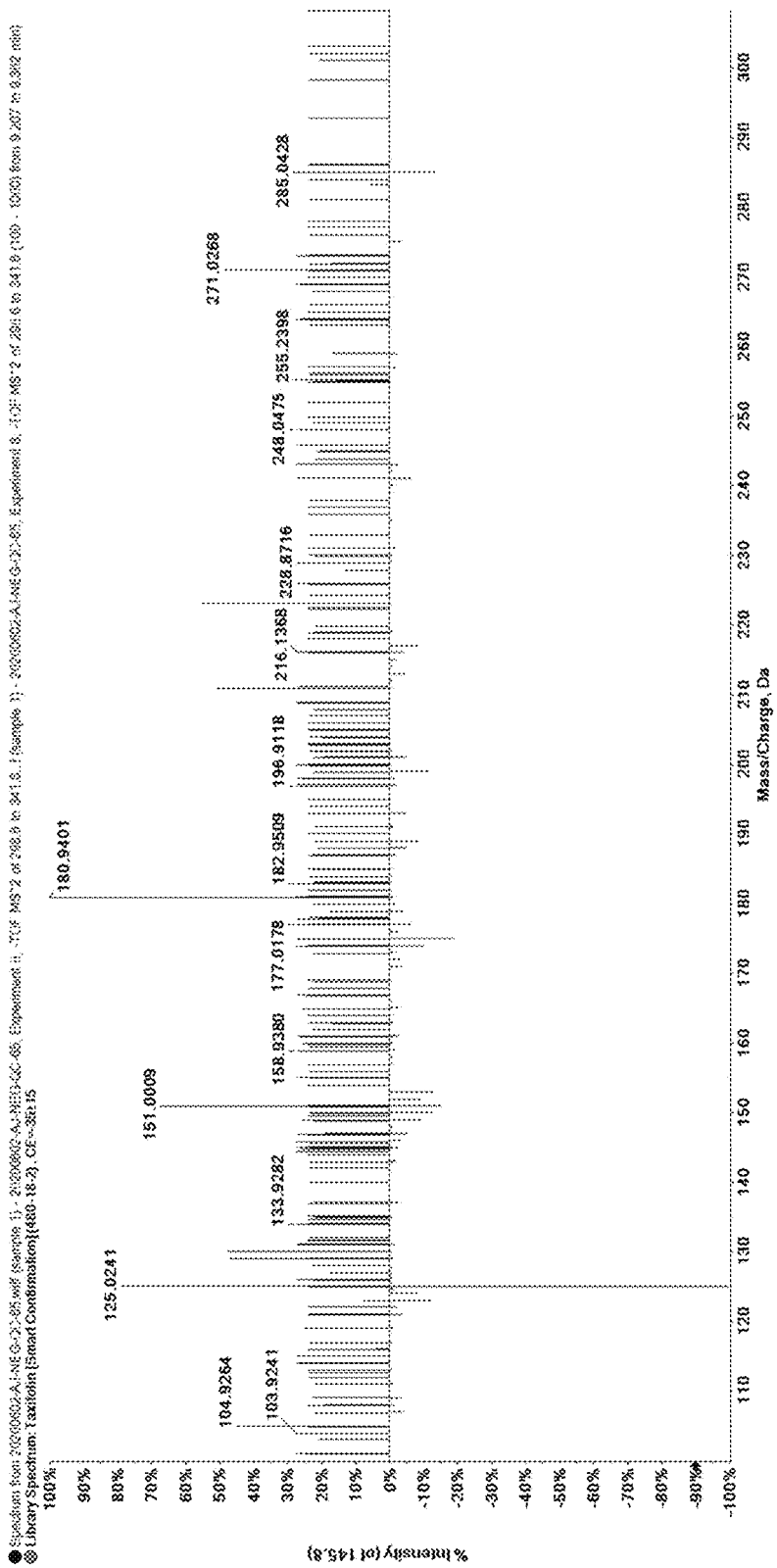
Figure 8:
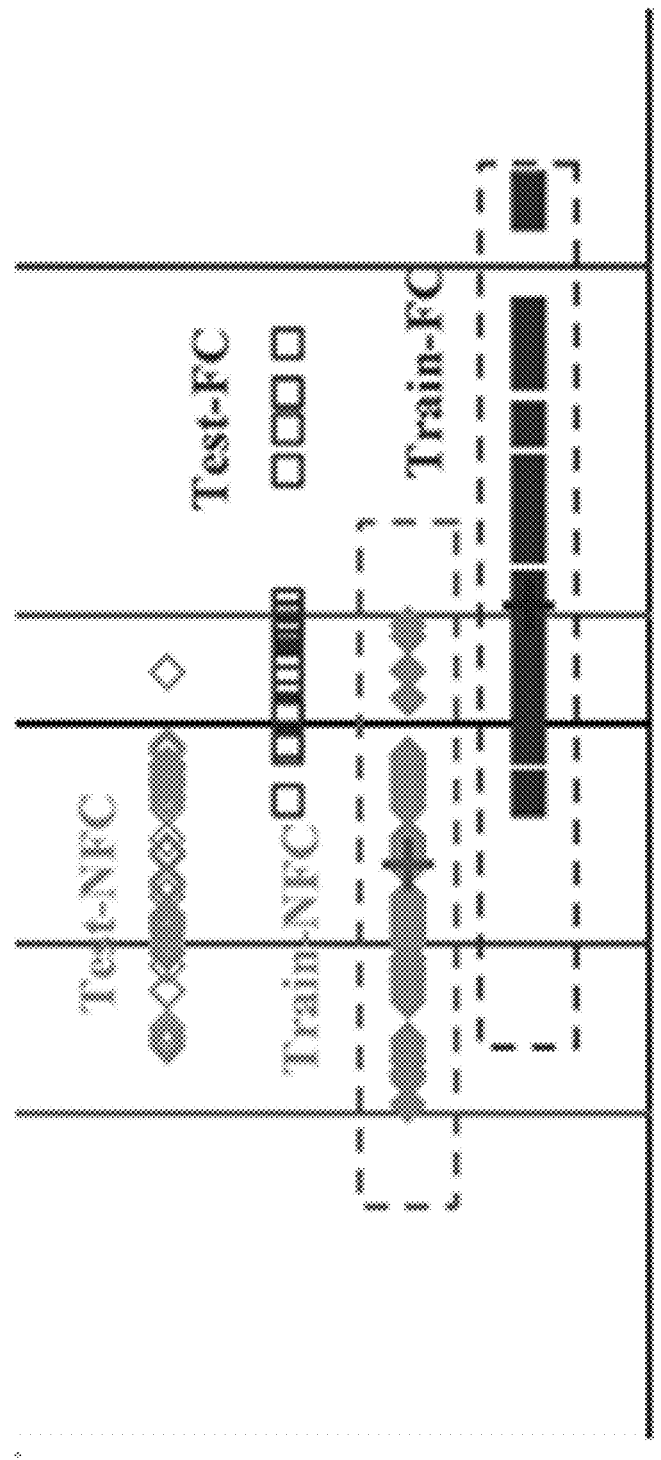
Figure 9:
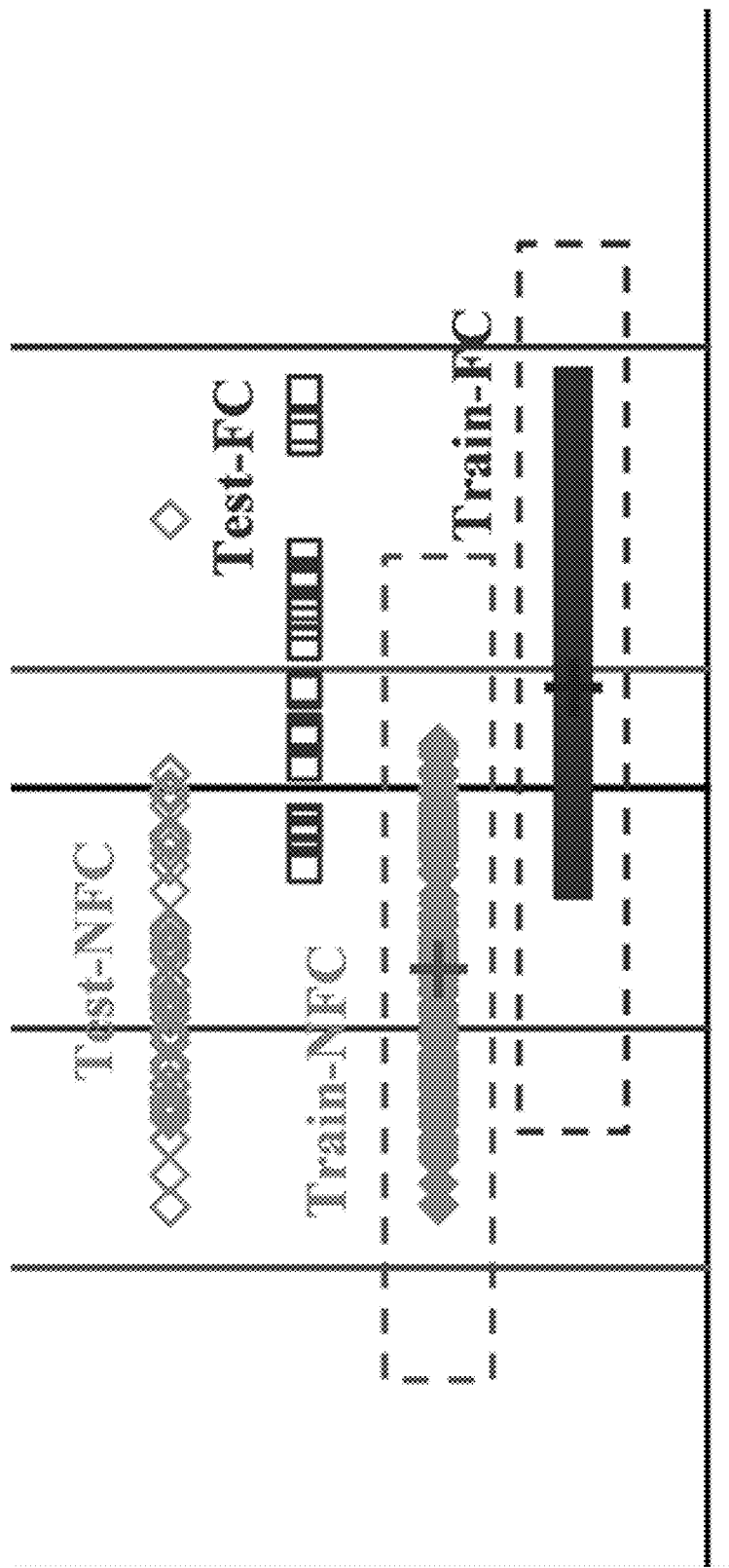
Figure 10:
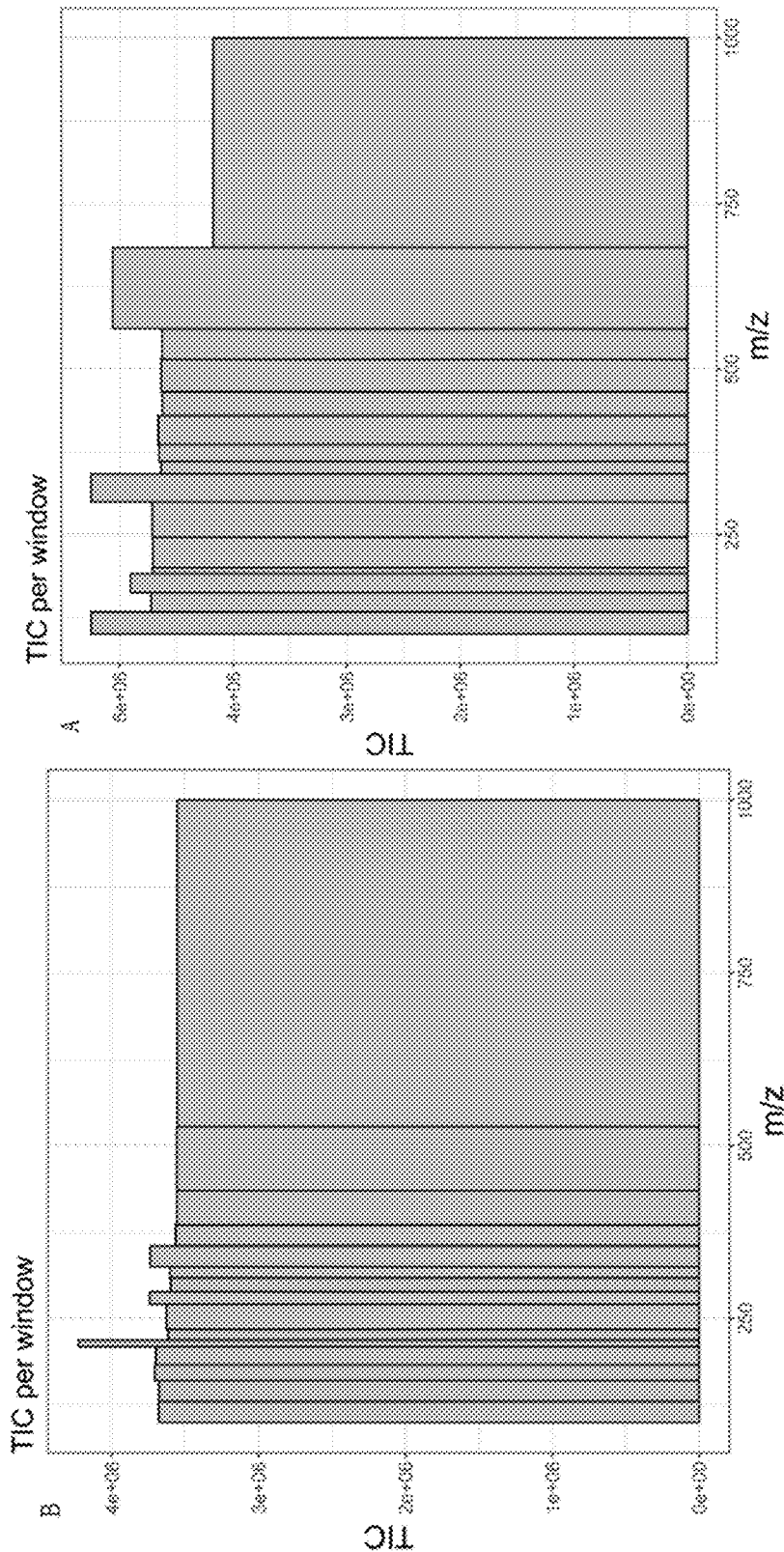

The experimental parameters of the TOF MS scan in positive ion mode were set as follows: curtain gas was 25, ion source gas 1 was 50, ion source gas 2 was 50, an ion source temperature was 500° C., an ion source spray voltage (ion spray voltage floating) was 5.5 kV, a declustering potential was 60 V; collision energy was 10 eV. The SWATH mode (cycle time was 545 ms) consisted of TOF MS scan (accumulation time was 50 ms) and a series of MS2 scanning windows (including 15 variable Q1 windows calculated according to total ion flow) in high sensitivity mode, as shown in FIG. 10; accumulation duration each time was 30 ms, the collision energy (CE) was 35 eV, and the collision energy spread (CES) was 15 eV, the MS1 accumulation range m/z was 100-1000, and the mass range m/z scanned by the MS2 was 50-1000.

In the negative ion mode, the curtain gas was 25, the ion source gas 1 was 50, the ion source gas 2 was 50, the ion source temperature was 500° C., the ion source spray voltage was −4.5 kV, the declustering potential was −60 V, the mass range of the MS1 scan is 100-1000, the collision energy was −10 eV, the mass range m/z of the MS2 scan was 50-1000, the collision energy was −35 eV, and the collision energy spread was 15 eV; and the remaining parameter settings were the same as those in the positive ion mode.

All samples were analyzed randomly, and at the same time, in order to ensure the stability and repetition of the system, a quality control sample (QC, made by mixing all samples in equal amounts) was inserted every 5 samples. Data accumulation was performed using Analyst TF1.7.1 (SCIEX, Redwood City, CA, USA).

Figure 2:
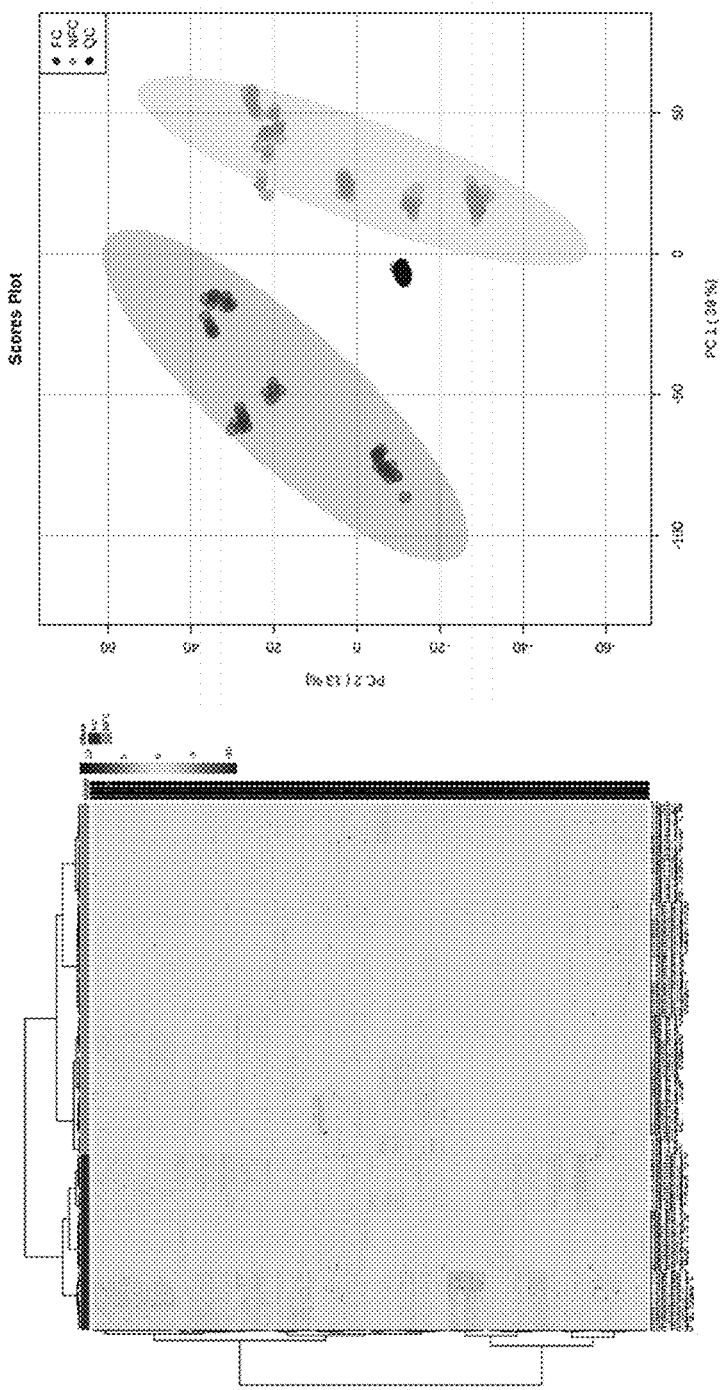
FIG. 2 is a PCA score plot (A) and heat map (B) of NFC apple juice and FC apple juice in the positive ion mode.
Figure 3:
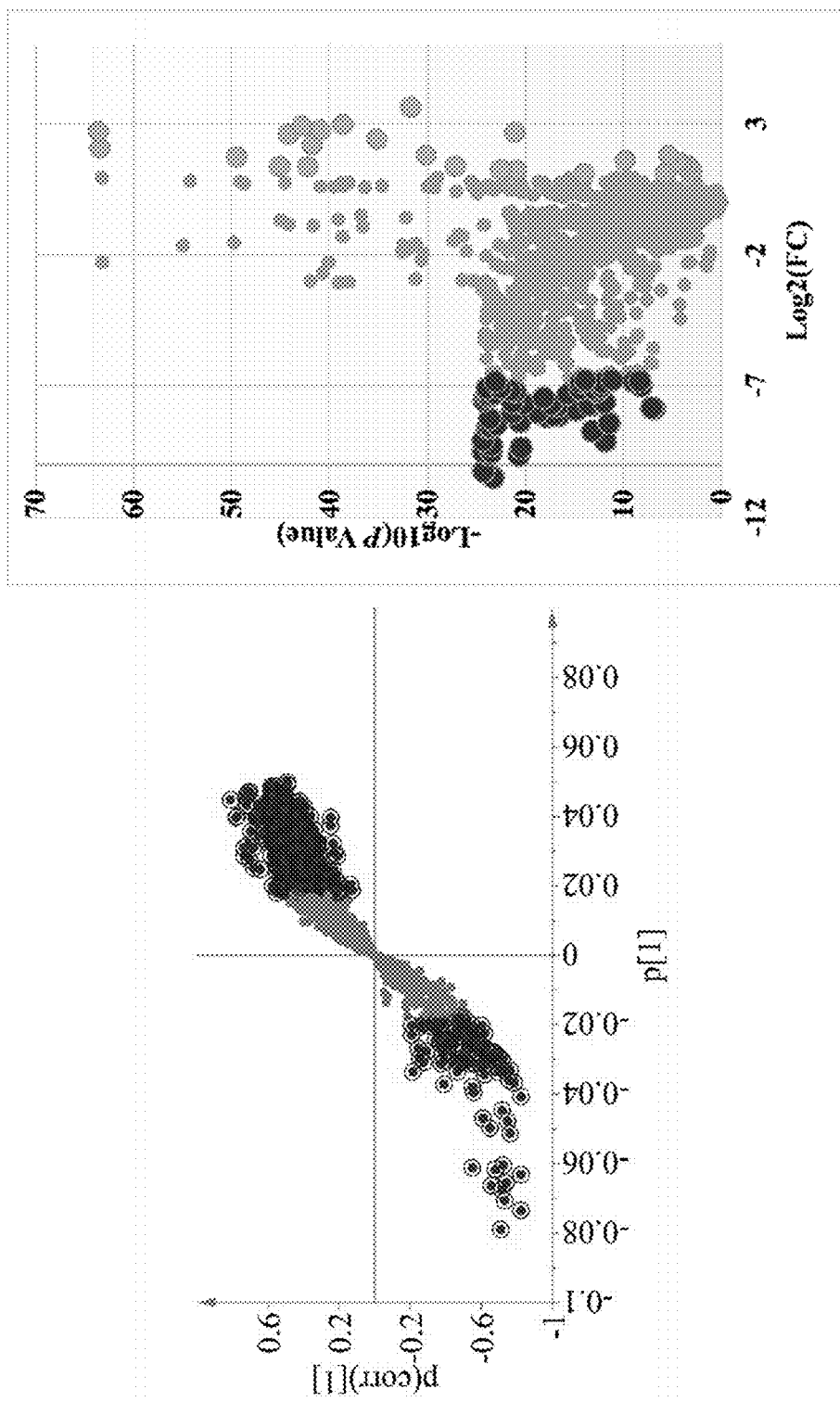
FIG. 3 is a volcano plot and S-plot of the NFC apple juice and the FC apple juice in the positive ion mode.
Figure 4:
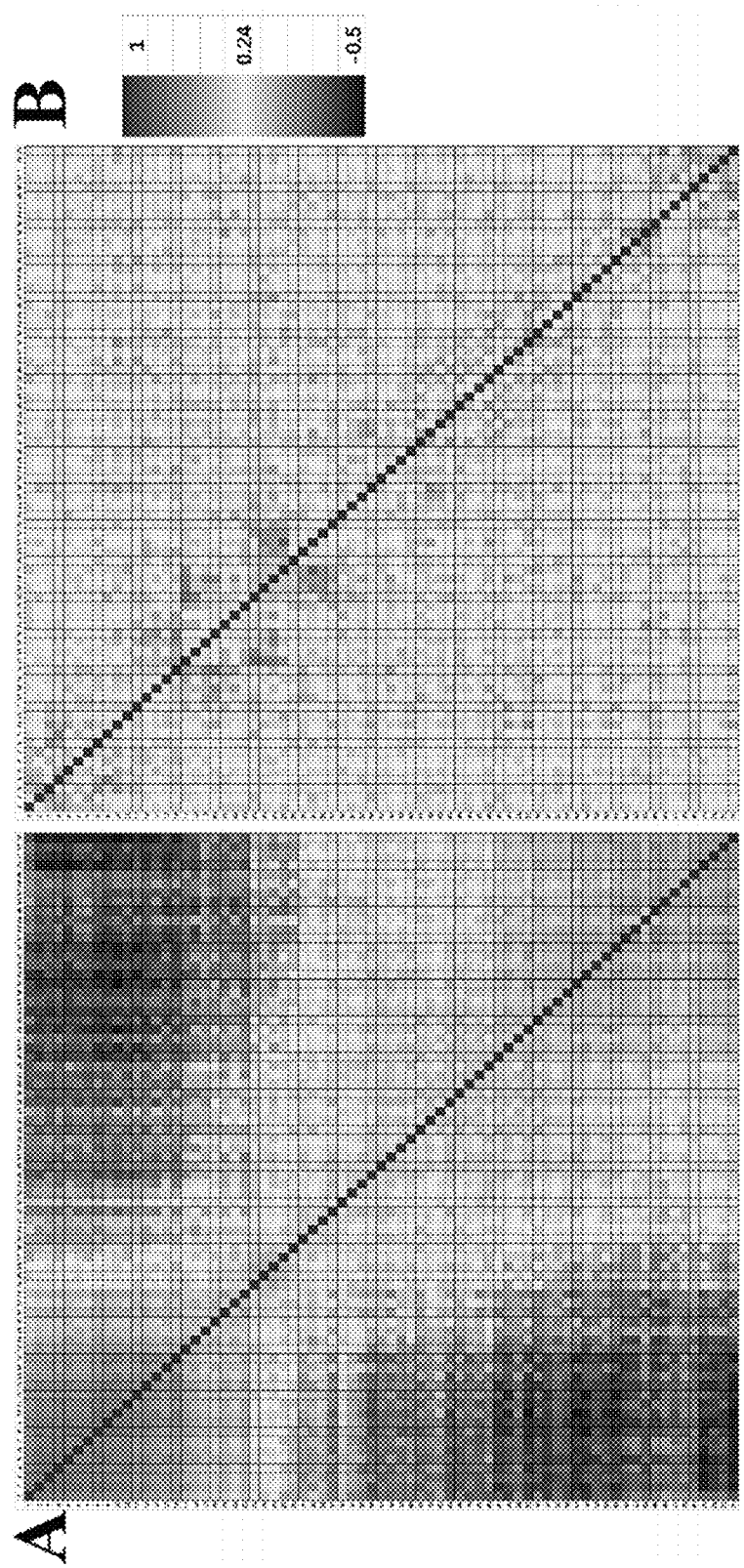
FIG. 4 is a correlation heat map of QC samples before and after correction in a negative ion mode; (A) is a correlation heat map of the QC samples before correction, and (B) is a correlation heat map of the QC samples after correction.
Figure 5:
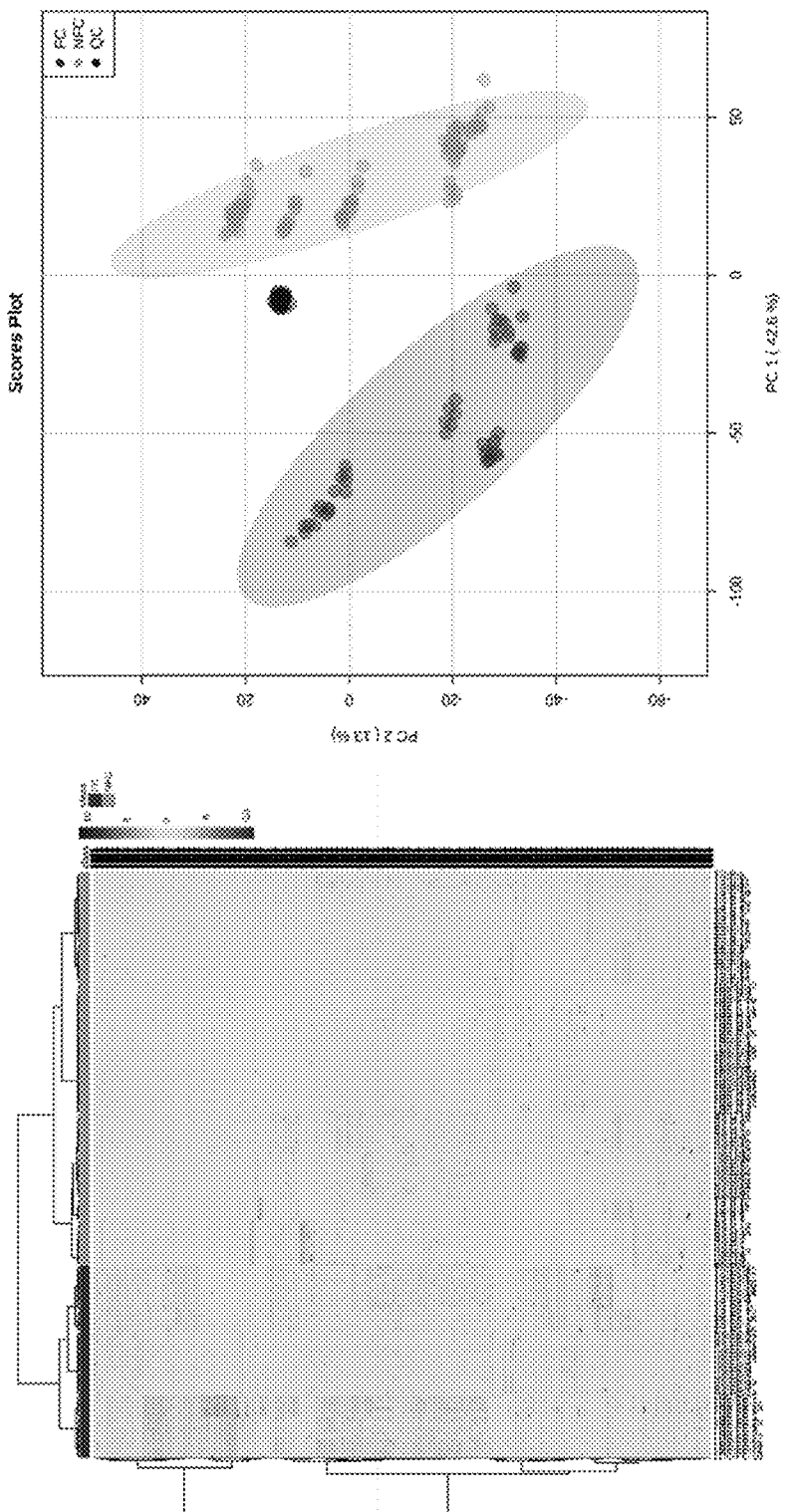
FIG. 5 is a PCA score plot (A) and heat map (B) of tge NFC apple juice and the FC apple juice in the negative ion mode.
Figure 6:
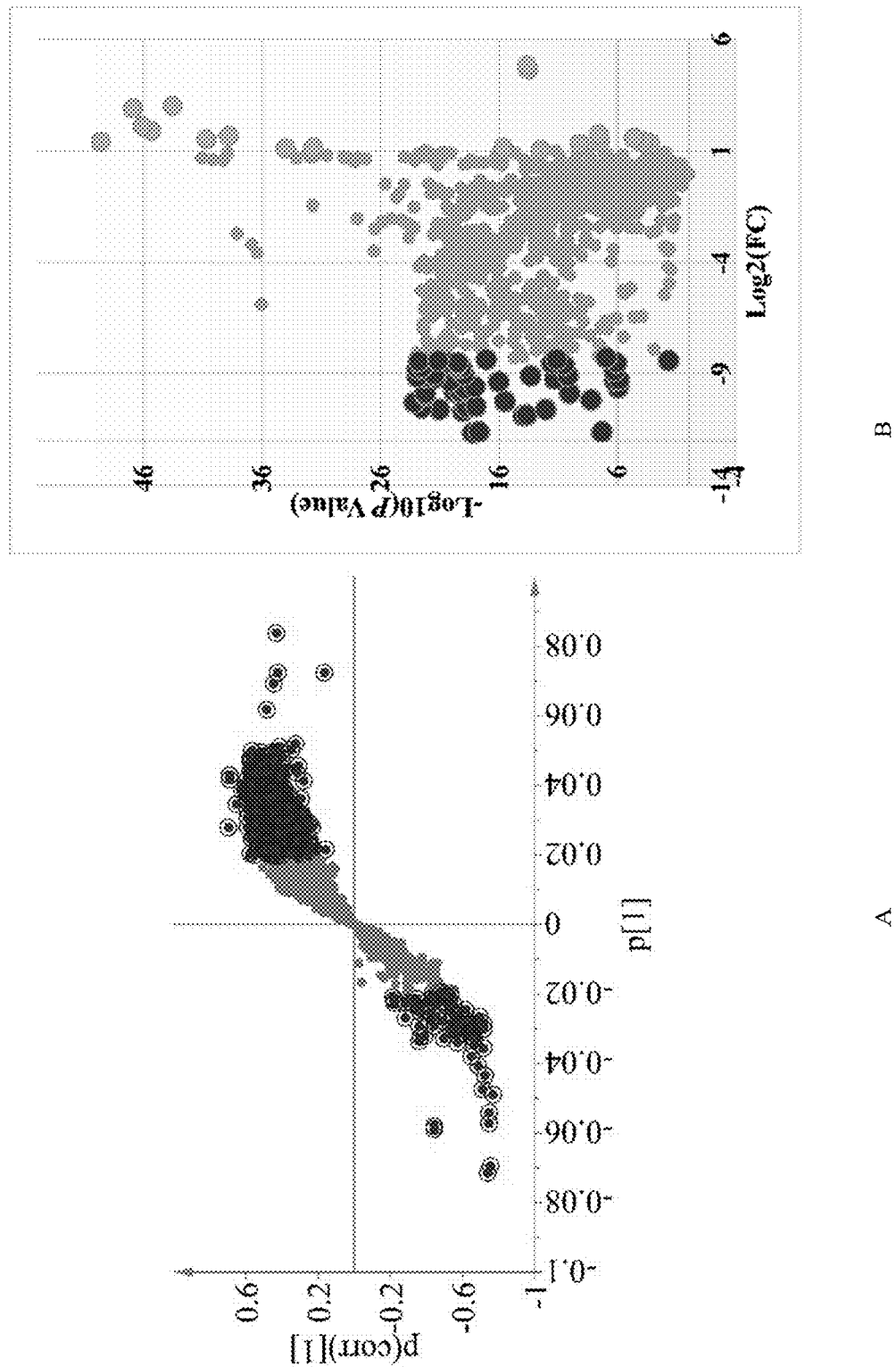
FIG. 6 is a volcano plot (A) and S-plot (B) of the NFC apple juice and the FC apple juice in the negative ion mode.

Peak extraction, peak alignment and list export were performed using MS-DIAL 4.36 software (RIKEN, Japan), and the parameters were set as: MS1 and MS2 tolerances were 0.01 Da and 0.025 Da, respectively, during peak extraction, the maximum charge number was 2, the MS1 and the MS2 tolerances qualitatively were 0.01 Da and 0.05 Da, respectively, the retention time deviation during peak alignment was 0.2 min, the MS1 deviation was 0.015 Da, and the chromatographic peak with a detection rate less than 80% in any group or a ratio of a maximum value in the samples to average in blank sample being less than 5 was removed. After the list was exported after the peak alignment, the response of each sample was responded based on the QC sample using a local weighted regression method, and the results in the positive and negative ion modes are shown in FIG. 1 and FIG. 4, respectively. Then, Microsoft Office Excel 2016 (Microsoft Corporation, Redmond, Washington, USA) software was used to perform detection rate (DR) and relative standard deviation (RSD) analysis on QC group data to delete compound of DR≤80% or RSD≥30%. Thereafter, the list was imported into MetaboAnalyst 4.0 (https://www.metaboanalyst.ca/) for principal component analysis (PCA) and hierarchical cluster analysis (HCA), and results in the positive and negative ion modes are shown in FIG. 2 and FIG. 5, respectively. Meanwhile, the Microsoft Office Excel 2016 software was used to perform the T-test analysis and differential fold change analysis, and the volcano plot was plotted. Finally, a potential variable orthogonal projection discrimination analysis (OPLS-DA) model was constructed after performing Par transformation on the data using SIMCA Version 14.1 (Umetrics, Sweden). Potential markers were found by p values in the T-test, a value of differential fold and variable importance of projection (VIP) values in the OPLS-DA model (p<0.05, fold change>2, VIP>1). The volcano plots and the S-plot results of the OPLS-DA model in the positive and negative ion modes are shown in FIG. 3 and FIG. 6, respectively. MS2 information of the potential markers acquired by SWATH were imported into MS-FINDER V3.24 software, and matched with built-in databases such as Massbank, GNPS, HMDB, and FooDB, to perform annotation analysis. Meanwhile, annotation analysis was performed using online databases such as MoNA (Massbank of North American) and METLIN. The parameters MS1 and MS2 tolerances were set to 10 ppm and 15 ppm, respectively. The potential markers were finally confirmed upon comparison of retention time and MS2 information by purchasing chemical analysis standards.

Through the accumulated metabonomics data of the apple juice samples, by screening the characteristic markers (p<0.05, VIP>1, fold change>2) using the OPLS-DA model and confirming the retention time and MS2 information of chemical analysis standards, it was found that there were in total 21 differentially expressed molecules in the two kinds of apple juice: gallocatechin, catechin, taxifolin, p-hydroxybenzaldehyde, 5-methoxysalicylic acid, azelaic acid, caffeic acid, chlorogenic acid, epicatechin, eriodictyol, ferulic acid, isoquercitrin, naringenin, n-fructosyl isoleucine, p-coumaraldehyde, p-coumaric acid, phloretin, phlorizin, procyanidin B1, quercetin-3-O-galactoside and rutin;

in the above, there were 14 molecules found to be differentially expressed in the positive ion mode, which were: gallocatechin, catechin, p-hydroxybenzaldehyde, caffeic acid, chlorogenic acid, epicatechin, isoquercitrin, n-fructosyl isoleucine, p-coumaric acid, phloretin, phlorizin, procyanidin B1, quercetin-3-O-galactoside and rutin;

there were 20 molecules found to be differentially expressed in the negative ion mode, which were: gallocatechin, catechin, taxifolin, p-hydroxybenzaldehyde, 5-methoxysalicylic acid, azelaic acid, caffeic acid, chlorogenic acid, epicatechin, eriodictyol, ferulic acid, isoquercitrin, naringenin, p-coumaraldehyde, p-coumaric acid, phloretin, phlorizin, procyanidin B1, quercetin-3-O-galactoside and rutin; and MS2 mirror images of the 21 differential molecules above are shown in FIGS. 7-1 to 7-21. The relevant information of mass-to-charge ratio of the 21 differential molecules above is shown in the preceding Table 1.

The above results may indicate that any one or a composition of more of the above 21 molecules screened out in the example may act as a marker for distinguishing NFC apple juice and FC apple juice.

Example 2

A PLS-DA model for distinguishing NFC apple juice and FC apple juice was established and constructed based on the 21 marker molecules in Example 1, which included:

centrifuging 199 apple juice samples in Example 1 in a centrifuge (26916 g, 4° C.) for 15 min, then filtering the supernatant on a PES membrane filter head of 0.45 and 0.22 μm, and then loading the resultant into a sample bottle as a sample for subsequent analysis; and accumulating data using an ultra-high performance liquid chromatography in combination with quadrupole time-of-flight high-resolution mass spectrometer. Specific parameters of the chromatography system were as follows: all samples were analyzed using an ExionLC ultra-high performance reversed phase liquid chromatography system (SCIEX, Redwood City, CA, USA), mobile phase A was 0.2% aqueous formic acid solution, B was acetonitrile, and the flow rate was 300 μL/min; a feeding volume was 2 μL; a chromatographic column was HSST3 (ACQUITYUPLC, 1.8 μm, 2.1100 mm, Waters, USA), and a column temperature was kept at 40° C.; and a mobile phase gradient was as follows:

0-11.50 min, 5%-30% B; 11.50-11.51 min, 30-100% B; 11.51-15.00 min, 100% B; 15.00-15.01 min, 100%-5% B; 15.01-18 min, 5% B.

Specific parameters of a mass spectroscopy system were as follows: the mass spectroscopy analysis was performed using a quadrupole time-of-flight (QTOF) high-resolution mass spectrometer (TripleTOF6600, SCIEX, Redwood City, CA, USA), and the TOF MS and MS2 of each sample were scanned in a mode of accumulating all theoretical fragment ions (SWATH) simultaneously from consecutive windows, and each accumulation cycle included 15 SWATH windows. The instrument was calibrated automatically by a calibration delivery system (CDS) (SCIEX, Redwood City, CA, USA) every 4 samples.

The experimental parameters of the TOF MS scan in the positive ion mode were set as follows: curtain gas was 25, ion source gas 1 was 50, ion source gas 2 was 50, an ion source temperature was 500° C., an ion spray voltage floating was 5.5 kV, a declustering potential was 60 V; collision energy was 10 eV. The SWATH mode (cycle time was 545 ms) consisted of TOF MS scan (accumulation time was 50 ms) and a series of MS2 scanning windows (including 15 variable Q1 windows calculated according to total ion flow with m/z of 100-1000) in high sensitivity mode; accumulation duration each time was 30 ms, the collision energy (CE) was 35 eV, and the collision energy spread (CES) was 15 eV, the MS1 accumulation range m/z was 100-1000, and the mass range m/z scanned by the MS2 was 50-1000. All samples were analyzed randomly, and at the same time, in order to ensure the stability and repetition of the system, a quality control sample (QC, made by mixing all samples in equal amounts) was inserted every 5 samples. LC-QTOF data accumulation was performed using Analyst TF1.7.1 (SCIEX, Redwood City, CA, USA).

In the negative ion mode, the curtain gas was 25, the ion source gas 1 was 50, the ion source gas 2 was 50, the ion source temperature was 500° C., the ion source spray voltage was −4.5 kV, the declustering potential was −60 V, the mass range of the MS1 scan was 100-1000, the collision energy was −10 eV, the mass range m/z of the MS2 scan was 50-1000, the collision energy was −35 eV, and the collision energy spread was 15 eV; and the remaining parameter settings were the same as those in the positive ion mode. The peak areas of the 21 marker molecules screened out in Example 1 were extracted from the data in the positive and negative ion modes, respectively (wherein there were 14 marker molecules in the positive ion mode: gallocatechin, catechin, p-hydroxybenzaldehyde, caffeic acid, chlorogenic acid, epicatechin, isoquercitrin, n-fructosyl isoleucine, p-coumaric acid, phloretin, phlorizin, procyanidin B1, quercetin-3-O-galactoside and rutin; and there were 20 marker molecules in the negative ion mode: gallocatechin, catechin, taxifolin, p-hydroxybenzaldehyde, 5-methoxysalicylic acid, azelaic acid, caffeic acid, chlorogenic acid, epicatechin, eriodictyol, ferulic acid, isoquercitrin, naringenin, p-coumaraldehyde, p-coumaric acid, phloretin, phlorizin, procyanidin B1, quercetin-3-O-galactoside and rutin, and the peak areas of the corresponding markers in each sample was obtained and imported into Excel to establish a data partial least squares discrimination analysis (PLS-DA) model. The data modeling parameters in the positive ion mode were: the number of principal components (PC) was 2, the Type I error was 0.01, and the outliers' significance was 0.05. The data modeling parameters in the negative ion mode were: the number of principal components (PC) was 10, the Type I error was 0.01, and the outliers' significance was 0.05. Positive ion mode PLS-DA model and negative ion mode PLS-DA model for distinguishing the NFC apple juice and the FC apple juice based on the above marker contents were obtained, respectively.

Upon verification, the accuracy of the correction set of the PLS-DA model established in the above positive ion mode reached 95% (see FIG. 8), respectively. The accuracy of the correction set of the PLS-DA model established in the negative ion mode reached 88% (see FIG. 9). It should be noted that, in other examples, only the positive ion mode or the negative ion mode may be selected to accumulate data to establish the distinguishing model.

Example 3

The samples to be tested were actually distinguished using the PLS-DA model in Example 2.

A method of identifying apple juice samples to be distinguished using the PLS-DA model for distinguishing NFC apple juice and FC apple juice in Example 2 was as follows:

(1) taking 71 apple juice samples unused in Example 2 as the apple juice samples to be distinguished, centrifuging the apple juice samples to be distinguished in a centrifuge (26916 g, 4° C.) for 15 min, then filtering the supernatant on a PES membrane filter head of 0.45 μm and 0.22 μm, and then loading the resultant into a sample bottle as a sample for subsequent analysis; and accumulating data using an ultra-high performance liquid chromatography in combination with quadrupole time-of-flight high-resolution mass spectrometer. Specific parameters of the chromatography system were as follows: all samples were analyzed using an ExionLC ultra-high performance reversed phase liquid chromatography system (SCIEX, Redwood City, CA, USA), mobile phase A was 0.2% aqueous formic acid solution, B was acetonitrile, and the flow rate was 300 μL/min; a feeding volume was 2 μL; a chromatographic column was HSST3 (ACQUITYUPLC, 1.8 μm, 2.1*100 mm, Waters, USA), and a column temperature was kept at 40° C.; and a mobile phase gradient was as follows:

0-11.50 min, 5%-30% B; 11.50-11.51 min, 30-100% B; 11.51-15.00 min, 100% B; 15.00-15.01 min, 100%-5% B; 15.01-18 min, 5% B.

Specific parameters of a mass spectroscopy system were as follows: the mass spectroscopy analysis was performed using a quadrupole time-of-flight (QTOF) high-resolution mass spectrometer (TripleTOF6600, SCIEX, Redwood City, CA, USA), and the TOF MS and MS2 of each sample were scanned in a mode of accumulating all theoretical fragment ions (SWATH) simultaneously from consecutive windows, and each accumulation cycle included 15 SWATH windows. The instrument was calibrated automatically by a calibration delivery system (CDS) (SCIEX, Redwood City, CA, USA) every 4 samples.

The experimental parameters of the TOF MS scan in the positive ion mode were set as follows: curtain gas was 25, ion source gas 1 was 50, ion source gas 2 was 50, an ion source temperature was 500° C., an ion spray voltage floating was 5.5 kV, a declustering potential was 60 V; collision energy was 10 eV. The SWATH mode (cycle time was 545 ms) consisted of TOF MS scan (accumulation time was 50 ms) and a series of MS2 scanning windows (including 15 variable Q1 windows calculated according to total ion flow with m/z of 100-1000) in high sensitivity mode; accumulation duration each time was 30 ms, the collision energy (CE) was 35 eV, and the collision energy spread (CES) was 15 eV, the MS1 accumulation range m/z was 100-1000, and the mass range m/z scanned by the MS2 was 50-1000. All samples were analyzed randomly, and at the same time, in order to ensure the stability and repetition of the system, a quality control sample (QC, made by mixing all samples in equal amounts) was inserted every 5 samples. LC-QTOF data accumulation was performed using Analyst TF1.7.1 (SCIEX, Redwood City, CA, USA).

In the negative ion mode, the curtain gas was 25, the ion source gas 1 was 50, the ion source gas 2 was 50, the ion source temperature was 500° C., the ion source spray voltage was −4.5 kV, the declustering potential was −60 V, the mass range of the MS1 scan was 100-1000, the collision energy was −10 eV, the mass range m/z of the MS2 scan was 50-1000, the collision energy was −35 eV, and the collision energy spread was 15 eV; and the remaining parameter settings were the same as those in the positive ion mode.

In the positive and negative ion modes, respectively, the peak areas of the above markers of samples were extracted, wherein there were 14 markers in the positive ion mode, and 20 markers in the negative ion mode, and the peak areas were imported into the PLS-DA model established in the corresponding ion mode established in Example 2. Upon detection, the accuracy of the prediction set of the PLS-DA model established in the positive ion mode through the above steps reached 94% (see FIG. 8); and the accuracy of the prediction set of PLS-DA model established in negative ion mode was 88% (see FIG. 9).

In summary, the fruit and vegetable juice counterfeit distinguishing technology is an important means for ensuring the quality and safety of the fruit and vegetable juice. Although our country has developed highly effective counterfeit distinguishing research at present, the counterfeit distinguishing technology applied to practical production is still not mature enough. It is quite difficult to establish a pervasive fruit and vegetable juice counterfeit distinguishing technology due to the fact that the fruit and vegetable raw materials are closely related to regions, climates, varieties, water and soil, agricultural production and the like, and the differences between fruit and vegetable juice processing technologies. Furthermore, new fruit and vegetable juice products develop fast, but the corresponding supervisory system and detection technology are still not robust enough, and there are disadvantages from the standard of the raw materials, to the production technology specification, and then to the means for identifying the authenticity of the products. Therefore, it is impossible to implement effective protection on the booming market of new fruit and vegetable juice. The method according to the examples of the present disclosure can carry out the research of the raw material characteristic index of regional characteristics according to the actual situation of our country, and the research of the characteristic index of different processing technologies according to the fruit and vegetable juice processing technology. The apple juice counterfeit distinguishing technology with differentiated indices is established based on the modern foodomics method, which may provide strong protection for improving the technical system urgently needed for new juice, realizing product quality certification, strengthening supervision and inspection, and promoting production upgrades.

The above-mentioned are merely for preferred examples of the present disclosure but are not used to limit the present disclosure. For one skilled in the art, various modifications and changes may be made to the present disclosure. Any amendments, equivalent replacements, improvements, and so on, within the spirit and principle of the present disclosure, should be covered within the scope of protection of the present disclosure.

What is claimed is:

1. A method for distinguishing NFC apple juice and FC apple juice, wherein the method comprises:
    detecting a content of at least one marker in an apple juice sample to be distinguished; and judging whether the apple juice sample to be distinguished is NFC apple juice or FC apple juice according to the content of the marker,
    wherein the judging comprises: substituting the content of at least one marker of the apple juice sample to be distinguished into a distinguishing model for distinguishing, wherein the distinguishing model is a PLS-DA model constructed according to contents of the at least one marker in an NFC apple juice sample and a FC apple juice sample,
    wherein contents of the at least one marker in the sample to be distinguished, the NFC apple juice sample and the FC apple juice sample are detected by a chromatographic technique, a mass-spectrometric technique or a combination thereof,
    wherein the PLS-DA model is established according to content data of the at least one marker accumulated in a positive ion mode, and
    wherein the at least one marker is at least one selected from following markers: gallocatechin, catechin, p-hydroxybenzaldehyde, caffeic acid, chlorogenic acid, epicatechin, isoquercitrin, n-fructosyl isoleucine, p-coumaric acid, phloretin, phlorizin, procyanidin B1, quercetin-3-O-galactoside and rutin.

2. The method according to claim 1, wherein the content of the marker is detected by the chromatographic technique in combination with the mass-spectrometric technique, and the content of the marker is expressed by a peak area.

3. The method according to claim 2, wherein 2 or more NFC apple juice samples and 2 or more FC apple juice samples are used to construct the PLS-DA model.

4. The method according to claim 3, wherein a chromatographic condition used for detecting the content of the marker by the chromatographic technique in combination with the mass-spectrometric technique is as follows:

performing gradient elution with a mobile phase A and a mobile phase B, wherein the mobile phase A is 0.2% aqueous formic acid solution, the mobile phase B is acetonitrile, with a flow rate of 300 μL/min, and a feeding volume of 2 μL, wherein a condition of the gradient elution is as follows:
0-11.50 min, 5%-30% B; 11.50-11.51 min, 30-100% B; 11.51-15.00 min, 100% B; 15.00-15.01 min, 100%-5% B; 15.01-18 min, 5% B, wherein each numerical parameter fluctuates in a range of ±5%.

5. The method according to claim 3, wherein a mass-spectrometric condition used for detecting the content of the marker by the chromatographic technique in combination with the mass-spectrometric technique is as follows:

in the positive ion mode, flow rate of a curtain gas, an ion source gas 1, an ion source gas 2 is 25:50:50, an ion source temperature is 500° C., an ion source spray voltage is 5.5 kV, a declustering potential is 60 V, a mass range of an MS1 scan is 100-1000, a collision energy is 10 eV, a mass range of an MS2 scan is 50-1000, a collision energy is 35 eV, and a collision energy spread is 15 eV; and in the negative ion mode, a curtain gas is 25, an ion source gas 1 is 50, an ion source gas 2 is 50, an ion source temperature is 500° C., an ion source spray voltage is −4.5 kV, a declustering potential is −60 V, a mass range of the MS1 scan is 100-1000, a collision energy is −10 eV, a mass range of the MS2 scan is 50-1000, a collision energy is −35 eV, and a collision energy spread is 15 eV, wherein each numerical parameter fluctuates in a range of ±5%.

6. The method according to claim 3, wherein parameters are set as follows: principle components are in a number of 2, Type I error is 0.01, and outliers' significance is 0.05.

* * * * *